(12) United States Patent
Woods

(10) Patent No.: US 7,033,615 B2
(45) Date of Patent: Apr. 25, 2006

(54) METHODS FOR REGULATING LEVELS OF ZINC, CADMIUM AND CALCIUM IN HUMANS AND FOR DIAGNOSING, OR SCREENING FOR THE RISK OF DEVELOPING, DISEASES ASSOCIATED WITH ABNORMAL LEVELS OF CADMIUM, ZINC AND CALCIUM IN BODY FLUIDS AND TISSUES

(75) Inventor: Gordon L. Woods, Moscow, ID (US)

(73) Assignee: CancEr2 Inc., Moscow, ID (US)

( * ) Notice: Subject to any disclaimer, the term of this patent is extended or adjusted under 35 U.S.C. 154(b) by 277 days.

(21) Appl. No.: 09/989,674

(22) Filed: Nov. 21, 2001

(65) Prior Publication Data

US 2002/0114848 A1 Aug. 22, 2002

Related U.S. Application Data

(63) Continuation-in-part of application No. 09/610,538, filed on Jul. 7, 2000.

(60) Provisional application No. 60/142,926, filed on Jul. 9, 1999.

(51) Int. Cl.
*A61K 33/24* (2006.01)
*A61K 33/32* (2006.01)
*A61K 33/14* (2006.01)
*A61K 33/06* (2006.01)

(52) U.S. Cl. ............... 424/654; 424/641; 424/678; 424/682

(58) Field of Classification Search ........... 424/654, 424/641, 678, 682
See application file for complete search history.

(56) References Cited

U.S. PATENT DOCUMENTS 4,225,592 A * 9/1980 Lakatos et al. ............... 514/54
5,130,298 A * 7/1992 Cini et al. .................... 514/12
5,994,337 A 11/1999 Washburn et al.

FOREIGN PATENT DOCUMENTS

WO   WO 88/03805 A1   6/1988
WO   WO 96/06836 A2   3/1996

OTHER PUBLICATIONS

Jacobson et al. British Journal of Nutrition, (Jan. 1977) 37 (1) 107-26.*
"Cadmium oxide" EPA Chemical Profiles, United States Environmental Protection Agency, Washington D.C. 20460, USA, Dec. 1985. 4p.*
Nordberg et al. IARC Scientific Publications, (1992) vol. 118, No. Cadmium in the Human Environment, pp. 293-297.*
Waalkes, Michael P. et al., "Further evidence of the tumor-suppressive effects of cadmium in the B6C3F mouse liver and lung: Late state vulnerabiliy of tumors to cadmium and the role of metallothionein," *J. Pharmacol. Exp. Ther* (1993), 266(3), 1656-63.
Lee, Kang Bo et al., "Effect of cadmium on human ovarian cancer cells with acquired cisplatin resistance," *Cancer Lett.* (Shannon, Ireland) (1995), 88(1), 57-66.
Waalkes, Michael P., "Anticarcinogenic effects of cadmium in review," *Met. Ions Biol. Med., Proc. Int. Symp. 3rd* (1994), 137-42, Editors: Collery, Philippe, Publisher: Libbey, Montrouge, France.
Waalkes, Michael P., "Down-regulation of metallothionein expression in human and murine hepatocellular tumors: association with the tumor-necrotizing and antineoplastic effects of cadmium in mice," *J. Pharmacol. Exp. Ther.* (1996), 277(2), 1026-1033.
Gachot et al., "Effects of Cadmium and Copper on Zinc Transport Kinetics by Isolated Renal Proximal Cells," *Biol. Trace Elem. Res.*, 35(2):93-103, 1992.
Watanabe et al., "Correlation of Cadmium, Copper, Manganese, and Zinc Levels in the Urine of People in Nonpolluted Areas," *J. Toxicol Environ. Health*, 33(3):263-72, 1991.
Moon J., "The Role of Vitamin D in Toxic Metal Absorption: A Review," *J. Am. Coll. Nutr.*, 13(6):559-64, 1994.
Nomiyama et al., "Trace Elements in Cardio-Cerebrovascular Diseases," *Ann. N. Y. Acad. Sci.*, 676:308-26, 1993.
Ozdem et al., "The Effects of Short-Term Nifedipine Treatment on Responsiveness of Aortic Rings of Cadmium-Hypertensive Rats," *Clin. Exp. Hypertens.*, 21(4):423-40, 1999.
Pandya et al., "Accumulation and Interrelationship of Cadmium and Zinc in Human Kidney Cortex," *Environ. Res.*, 36(1):81-8, 1985.
Torra et al., "Cadmium and Zinc Relationships in the Liver and Kidney of Humans Exposed to Environmental Cadmium," *Sci. Total Environ.*, 170(1-2):53-7, 1995.
Whelton et al., "Hepatic Levels of Cadmium, Zinc and Copper in Multiparous, Nulliparous and Ovariectomized Mice fed either a Nutrient-Sufficient or -Deficient Diet Containing Cadmium," *Toxicology*, 119(2):141-53, 1997.

(Continued)

*Primary Examiner*—Shaojia Anna Jiang
(74) *Attorney, Agent, or Firm*—Rothwell, Figg, Ernst & Manbeck PC

(57) ABSTRACT

Methods and compositions are provided for decreasing PGE2:PGF2α, regulating ratios of zinc:cadmium and regulating the concentration of zinc, calcium and zinc-containing and PGE2-dependent matrix metalloproteinases in body fluids and tissues of a human. Elevated or otherwise unregulated levels of PGE2, zinc and calcium and elevated concentrations of zinc-containing and PGE2-dependent matrix metalloproteinases have been found to be associated with the development of certain diseases.

14 Claims, No Drawings

OTHER PUBLICATIONS

Koizumi, "Relationship of Cadmium Accumulation to Zinc or Copper Concentration in Horse Liver and Kidney" *Environmental Research* 49:104-114, 1989.

Vivoli et al., "Cadmium in Blood, Urine and Hair Related to Human Hypertension," *J. Trace Elem. Electrolytes Health Dis.*, 3:139-145, 1989.

Elinder et al., "Cadmium and Zinc Relationships," *Environmental Health Perspectives*, 25:129-132, 1978.

Foulkes, E. C., "Interactions Between Metals in Rat Jejunum: Implications on the Nature of Cadmium Uptake," *Toxicology*, 37:117-125, 1985.

Visser et al., "Cadmium Ion is a Non-Competitive Inhibitor of Red Cell $Ca^{2+}$-ATPase Activity," *Biochimica et Biophysica Acta*, 1152:26-34, 1993.

Gerard, J.P. et al., "Curative external beam radiotherapy for prostate carcinoma: results in 231 patients treated in Lyon," Aust. N. Z. J. Surg., 69(10):707-711 (1999).

Fortier, A.H. et al., "Antiangiogenic activity of prostate-specific antigen," J. Natl. Cancer Inst., 91(19):1635-1640 (1999).

Tremblay, C. et al., "Induction of prostaglandin G/H synthase-2 in a canine model of spontaneous prostatic adenocarcinoma," J. Natl. Cancer Inst., 91(16):1398-1403 (1999).

Liang, J.Y. et al., "Inhibitory effect of zinc on human prostatic carcinoma cell growth," Prostate, 0(3):200-207 (1999).

Garfinkel, L. and Mushinski, M., "U.S. cancer incidence, mortality and survival: 1973-1996," Stat. Bull. Metrop. Insur. Co., 80(3):23-32 (1999).

Will, J.C. et al., "Is diabetes mellitus associated with prostate cancer incidence and survival," Epidemiology, 10(3):313-318 (1999).

Roberts, R.O. et al., "Decline in prostate cancer mortality form 1980 to 1997, and an update on incidence trends on Olmsted County, Minnesota," J. Urol., 161(2):529-533 (1999).

Hebert, J.R. et al., "Nutritional and socioeconomic factors in relation to prostate cancer mortality: a cross-national study," J. Natl. Cancer Inst., 90(21):1637-1647 (1998).

Kakehi, Y., "[Epidemiology and clinical features of prostate cancer in Japan]," Nippon Rinsho, 56(8):1969-1973 (1998).

Zaichick, V.Y. et al., "Zinc In the human prostate gland: normal, hyperplastic and cancerous," Int. Urol. Nephrol., 29(5):565-574 (1997).

Brys, M. et al., "Zinc and cadmium analysis in human prostate neoplasms," Biol. Trace Elem. Res., 59(1-3):145-152 (1997).

Shibata, A. et al., "Serum levels of prostate-specific antigen among Japanese-American and Native Japanese men" J. Natl. Cancer Inst., 89(22):1716-1720 (1997).

Andersson, S.O. et al., "Energy, nutrient intake and prostate cancer risk: a population-based case-control study in Sweden," Int. J. Cancer, 68(6):716-722 (1996).

Waalkes, M.P. et al., "Cadmium exposure in rats and tumors of the prostate," IARC Sci. Publ., (118):391-400 (1992).

Picurelli, L. et al., "[Determination of Fe, Mg, Cu, and Zn in normal and pathological prostatic tissue],"Actas. Urol. Esp., 15(4):344-350 (1991).

Wynder, E.L. et al., "Comparative epidemiology of cancer between the United States and Japan. A Second look." Cancer, 67(3):746-763 (1991).

Tsugane, S. et al., "Cancer incidence rates among apanese immigrants in the city of Sao Paulo, Brazil, 1969-1978," Cancer Causes Control, 1(2):189-193 (1990).

Tsugane, S. et al., "Cancer mortality among Japanese residents of the city of Sao Paulo, Brazil," Int. J. Cancer, 45(3):436-439 (1990).

Elqhany, N.A. et al., "Occupation, cadmium exposure, and prostate cancer," Epidemiology, 1(2):107-115 (1990).

Ogunlewe, J.O. and Osegbe, D.N., "Zinc and cadmium concentrations in indigenous blacks with normal, hypertrophic, and malignant prostate," Cancer, 63(7):1388-1392 (1989).

Kolonel, L.N. et al., "Diet and prostatic cancer: a case-control study in Hawaii," Am. J. Epidemiol., 127(5):999-1012 (1988).

Elinder, C.G. et al., "Cancer mortality of cadmium workers," Br. J. Ind. Med., 42(10):651-655 (1985).

Hoffmann, L. et al., "Carcinogenic effects of cadmium on the prostate of the rat," J. Cancer Res. Clin. Oncol., 109(3): 193-199 (1985).

Feustel, A. and Wennrich, R., "Determination of the distribution of zinc and cadmium in cellular fractions of BPH, normal prostate and prostatic cancers of different histologies by atomic and laser absorption spectrometry in tissue slices," Urol. Res., 12(5):253-256 (1984).

Feustel, A. and Wennrich, R., "Zinc and cadmium in cell fractions of prostatic cancer tissues of different histological grading in comparison to BPH and normal prostate," Urol. Res., 12(2):147-150 (1984).

Whelan, P. et al., "Zinc, vitamin A and prostatic cancer," Br. J. Urol., 55(5):525-528 (1983).

Feustel, A. et al., "Zinc and cadmium concentration in prostatic carcinoma of different histological grading in comparison to normal prostate tissue and adenofibromyomatosis (BPH)," Urol. Res., 10(6):301-303 (1982).

Niijima, T. and Koiso, K., "Incidence of prostatic cancer in Japan and Asia," Scand. J. Urol. Nephrol. Suppl., 55:17-21 (1980).

Dunn, J.E., "Cancer epidemiology in populations of the United States—with emphasis on Hawaii and California—and Japan," Cancer Res., 35(11 Pt.2):3240-3245 (1975).

Armenian, H.K. et al., "Epidemiologic characteristics of patients with prostatic neoplasms," Am. J. Epidemiol., 102 (1):47-55 (1975).

Willden, E.G. and Robinson, M.R., "Plasma zinc levels in prostatic disease," Br. J. Urol., 47(3):295-299 (1975).

Nielsen, Forrest H., "How Should Dietary Guidance Be Given for Mineral Elements with Beneficial Actions or Suspected of Being Essential?" *Dietary Guidance for Ultratrace Elements Supplement*, RDA Workshop: New Approaches, Endpoints and Paradigms for RDAs of Mineral Elements, 1996, pp. 2377S-2385S. American Institute of Nutrition.

Uthus, Eric O., "Deliberations and Evaluations of the Approaches, Endpoints and Paradigms for Dietary Recommendations of the Other Trace Elements," *Dietary Recommendations for Other Trace Elements*, RDA Workshop: New Approaches, Endpoints and Paradigms for RDAs of Mineral Elements, 1996, pp. 2452S-2459S. American Institute of Nutrition.

* cited by examiner

METHODS FOR REGULATING LEVELS OF ZINC, CADMIUM AND CALCIUM IN HUMANS AND FOR DIAGNOSING, OR SCREENING FOR THE RISK OF DEVELOPING, DISEASES ASSOCIATED WITH ABNORMAL LEVELS OF CADMIUM, ZINC AND CALCIUM IN BODY FLUIDS AND TISSUES

This patent application is a continuation-in-part of Ser. No. 09/610,538, filed Jul. 7, 2000, which claims priority from provisional patent application Ser. No. 60/142,926, filed Jul. 9, 1999.

FIELD OF THE INVENTION

The present invention relates to methods for regulating levels of cadmium, zinc and calcium in the human body. More specifically, the invention relates to methods for decreasing PGE2:PGF2α ratios and regulating zinc:cadmium ratios and for regulating the concentration of zinc-containing and PGE2-dependent matrix metalloproteinases in humans.

The invention further relates to methods of screening for the presence of, or risk of developing, a disease associated with unbalanced levels of cadmium in a body fluid, body fluid component or tissues of a human. The invention also relates to methods for delaying or preventing the onset of a disease in a human, wherein the disease is associated with unbalanced levels of cadmium and unregulated levels of zinc in body tissues and fluids, by balancing the levels of cadmium and regulating the levels of zinc in the body tissues and fluids of the human.

The invention further relates to methods for regulating the influx of extracellular calcium into cells and to methods for delaying or preventing the onset of a disease associated with above normal levels of intracellular calcium.

BACKGROUND OF THE INVENTION

Despite all the advances in medical treatment in recent years, a number of diseases remain difficult to treat. A number of these diseases are ones often associated with advancing age, although certainly they are not exclusively afflictions of the elderly. Cancers, for example, remain a leading cause of death in humans, despite advances in the field of cancer treatment. The leading therapies to date are surgery, radiation and chemotherapy. Many types of chemotherapeutic agents have shown at least some effectiveness against certain cancers and tumor cells, but the efficacy of these agents can vary significantly, and their side effects can be severe.

Hormones, in particular estrogen, progesterone and testosterone, and some antibiotics, alkylating agents, and antimetabolites form the bulk of therapeutic agents available to oncologists. Scientists continue to search for cytotoxic agents that have specificity for cancer and tumor cells, yet do not affect normal cells and have minimal side effects.

Other diseases which remain significant include hypertension, Alzheimer's disease, osteoporosis and diabetes.

Present treatments for diabetes include the administration of insulin either orally or through an injection solution. Also, glucose may be administered either directly, as through injection, or indirectly, as through ingestion of certain foods or drinks. Other methods of treating diabetes include the use of implantable glucose systems which have been designed to provide continuous measurement of the patient's glucose concentration. The use of implantable insulin pumps also can be used for the treatment of diabetes.

Such above described treatments for diabetes require lifelong treatment of the patient. For many patients insulin injection is an unpleasant process. Also the need for daily injections of insulin is hard on the patient's veins. Insulin treatment is costly and it is only a temporary reliever of diabetic symptoms. Continued treatment is necessary in order to control the disease. Therefore, there is a need for a remedy in treatment for diabetes which is easily administered to or by the patient.

Alzheimer's disease is believed to be an organic brain disease with primary invasions within the brain. Its etiology remains for the most part unknown. However, the current knowledge suggests that Alzheimer's disease is characterized by organic brain damage at least secondary to some preceding causative event. Current proposed treatments include the administration of substituted 1,4-benzoquinone derivatives including idebenone and corresponding hydroquinone derivatives. Current treatments have been of limited efficacy, and new and alternative treatments are sought.

Hypertension stresses the heart and can contribute to coronary artery disease, heart attack, and stroke. High blood pressure contributes to 75 percent of all strokes and it is estimated that half of all people who have a heart attack and two thirds of those who have a first stroke have high blood pressure. Over the past ten years, the number of deaths due to hypertension has increased by forty percent. Persons with hypertension often are advised to make lifestyle changes, such as diet and exercise and can be given various types of medications, including diuretics, alpha blockers and beta blockers, ACE inhibitors, and calcium channel blockers. Although all of these medications can be helpful, they also can have undesirable side effects, and further treatments are sought.

Persons with osteoporosis suffer from their bones becoming porous due to the deterioration of bone tissue. Eighty percent of osteoporosis sufferers are women. It is estimated that eight million women in the U.S. alone have osteoporosis. One in two women over fifty will suffer an osteoporosis-related fracture in their lifetime. The disease also affects about two million men in the U.S., and one in eight men over fifty will suffer from an osteoporosis-related fracture.

There currently is no cure for osteoporosis. Current therapies work to slow the progression of the disease. Preventive measures include calcium supplementation and regular weight-bearing exercise. Treatments include the administration of either of two types of drugs, ones which slow or inhibit bone formation or drugs which accelerate bond formation. Additional effective treatments are sought.

Research into all of these diseases has indicated that unregulated levels of zinc, either per se or in the form of zinc-containing or PGE2-dependent matrix metalloproteinases in body fluids and tissues, are associated with the onset and/or advancement of these diseases. As a result, attempts have been made to inhibit or to regulate the concentration of zinc and these enzymes in the body.

Methods for inhibiting matrix metalloproteinases used in the past include the use of hydroxamic acid derivatives such as alpha-amino sulphonyl hydroxamic acids and carboxypeptidyl compounds. Natural products such as TIMP-1, TIMP-2 and alpha 2-macroglobulin also are known matrix metalloproteinase inhibitors.

Although these inhibitors have been of interest, other easily manufactured compounds and compositions which can regulate the concentrations of matrix metalloproteinases, zinc and cadmium in the body fluids and tissues of a patient are sought.

Also sought are new methods for screening persons to determine the presence of, or their risk of developing, one of these diseases.

SUMMARY OF THE INVENTION

In accordance with the present invention, methods and compositions are provided for decreasing PGE2:PGF2α and regulating zinc:cadmium ratios and regulating the concentration of zinc-containing and PGE2-dependent matrix metalloproteinases in the body of a human. Methods and compositions also are provided for regulating calcium levels in the fluids and tissues in the body of a human. Elevated or otherwise unregulated levels of PGE2, zinc and calcium and elevated or otherwise unregulated concentrations of zinc-containing and PGE2-dependent matrix metalloproteinases have been found to be associated with the development of certain diseases, including prostate cancer, colon cancer, breast cancer, Alzheimer's disease, hypertension, osteoporosis and diabetes. For example, studies have found that patients with diabetes typically have elevated levels of zinc in their urine (104), and osteoporosis also has been associated with increased urinary zinc excretion (101). Zinc levels also have been shown to be elevated in the red blood cells and urine of persons suffering from cardiovascular disease; there is a decreased movement of zinc out of red blood cells, an increased movement of zinc into red blood cells and an increased excretion of zinc from the body. By regulating the concentration of zinc and PGE2 in the person's body, one can delay or prevent the onset of, or treat the development of, these diseases. Furthermore, it has been found that changes in cadmium and zinc levels also are associated with changes in calcium levels in the body. As cadmium regulates zinc, both cadmium and zinc regulate calcium. Unbalanced levels of cadmium lead to unregulated levels of zinc, which in turn leads to unregulated levels of calcium.

It also has been discovered that populations which have a high incidence of diseases such as prostate or breast cancer, hypertension, diabetes, osteoporosis and Alzheimer's also often have diets low in cadmium and unbalanced levels of cadmium in their body fluids, components of body fluid and tissues. For instance, a number of studies have found that cadmium levels are low in the cerebrospinal fluid of Alzheimer's patients. Accordingly, further in accordance with the present invention, methods are provided for screening persons to determine an indication of the presence of, or their risk of developing, a disease associated with unbalanced levels of cadmium in their body fluids, body fluid components, and tissues.

In one embodiment of the invention, there is provided a method of decreasing the PGE2:PGF2α ratio in the body fluids and tissues of a human which comprises administering to the human one or more cadmium salts in an amount sufficient to lower the concentration of PGE2.

In another embodiment of the invention, there is provided a method of balancing the amount of cadmium in the body fluids and/or tissues of a human which comprises administering to the human one or more cadmium salts in an amount sufficient to balance the concentration of cadmium per se and to regulate the concentration of zinc relative to the concentration of cadmium in the body fluids and/or tissues of the human.

In another embodiment of the present invention, there is provided a method for regulating the zinc:cadmium ratio in the body fluid or tissues of a human which comprises regulating the concentration and activity of zinc in the body fluid of the human by administering to the human one or more cadmium salts.

In a further embodiment, there is provided a method of regulating the concentrations of zinc and zinc-containing and PGE2-dependent matrix metalloproteinases in a human by administering one or more cadmium salts.

In another embodiment of the present invention, there is provided a pharmaceutical composition comprising a pharmaceutically acceptable carrier and one or more cadmium salts, said composition being in oral dosage form, parenteral dosage form or inhalation dosage form.

In yet another embodiment of the invention, there is provided a pharmaceutical composition comprising a pharmaceutically acceptable carrier and one or more cadmium salts in combination with an estrogen, a protease inhibitor or a combination thereof.

In still yet another embodiment of the invention, there is provided a method for treating, or for delaying or preventing the onset of, cancer, particularly prostate, colon or breast cancer, which comprises decreasing the PGE2:PGF2α ratio and regulating the zinc:cadmium ratio in the body fluids and tissues of a person suffering from, or at risk of developing, cancer by administering an amount of one or more cadmium salts effective to inhibit or prevent the formation, growth, division or metastasis of cancer cells.

In still yet another embodiment of the invention, there is provided a method for treating, or for delaying or preventing the onset of, a disease in a human, the onset of which is associated with unregulated levels of zinc and/or unbalanced levels of cadmium in the body fluids and tissues of the human, which comprises administering one or more cadmium salts at dose levels effective to regulate the concentration of zinc or balance the concentration of cadmium in the body fluids of a human suffering from or at risk of developing such a disease.

In a further embodiment of this invention, there is provided a method for regulating the influx of extracellular calcium into cells in the body of a human which comprises administering cadmium to said human in an amount sufficient to regulate the flow of extracellular calcium into the person's cells. There further is provided a method for delaying or preventing the onset of a disease associated with above normal levels of intracellular calcium which comprises administering to a human having abnormally high levels of intracellular calcium a pharmaceutically acceptable and bioavailable cadmium salt in an amount sufficient to regulate said levels of intracellular calcium.

DETAILED DESCRIPTION OF THE INVENTION

It is known that stallions have low fertility (e.g. unsuccessful equine in vitro fertilization (1)) and approximately ⅓ the incidence of cancer mortality compared to humans or dogs (8% versus 24% or 23%, respectively (2, 3, 4, 5)). Also, prostate cancer has never been reported in the stallion. Stallions have high levels of unique estrogens (6, 7, 8, 9) paralleling the high levels of unique estrogens of pregnant mares. Stallions, in comparison to man, have a low testosterone:estrogen ratio (stallions 1:13, (10), men 9:1, (10)) which may regulate their postulated low seminal plasma PGE2:PGF2α concentrations and ratio (11, 12, 13, 14, 15, 16, 17). It also is known that stallion urine comprises cadmium in the form of cadmium sulfate, as well as protease inhibitors and other chemicals.

Prostaglandin E2 (PGE2) increases sperm quality (26, 27, 28, 29, 30, 31) and increases cancer cell division (32). It also is known that zinc increases sperm quality (39) and enhances cancer cell metastasis (40, 41, 42). Zinc is a key component of proteases that function in cancer cell metastasis (40, 41, 42). Zinc typically is retained in tissues for only a few days (18). Zinc is regarded as an essential metal. Zinc has a negative relationship with cadmium. Zinc decreases the amount of cadmium absorbed from the gut (18) and decreases the physiological effects of cadmium (43, 44, 45, 46, 47, 48, 49, 50, 51).

Cadmium has been classified as a non-essential element that previously has been considered a toxin and hypothesized to cause prostate cancer and hypertension in man (77). The basis for this hypothesis appears to have stemmed from what was interpreted as a higher incidence of prostate cancer in men who inhaled cadmium (80), evidence of high concentrations of cadmium in prostate cancer cells (81) and cadmium-induced prostate cancer in rats (82).

In contrast to possible evidence that the inhalation of large quantities of cadmium leads to an increased incidence of prostate cancer in man, there is no evidence that ingested cadmium increases the incidence of prostate cancer. To the contrary, in countries such as Japan, in which the typical diet contains foods which have relatively high amounts of cadmium (83), the incidence of prostate cancer is very low (84). Conversely, Sweden, where cadmium ingestion is relatively low (85), has one of the highest incidences of prostate cancer in the world (86). As Japanese men have moved to western countries and shifted to low-cadmium western diets, their incidence of prostate cancer has been found to increase to levels similar to those of men in the same geographic areas (87). Similarly, Japanese men who have remained in Japan but changed to a low cadmium western diet, have shown an increase in their incidences of prostate cancer (88), whereas men in Sweden and the United States who shifted to more eastern-style diets, containing more cadmium, have shown a decrease in their incidence of prostate cancer (89).

Furthermore, the Internationale Programme on Chemical Safety stated in 1992 that the evidence to date regarding cadmium as a cause of prostate cancer is inconclusive but does not support the suggestion from earlier studies of a causal relationship and that there was no convincing evidence that cadmium is an etiological agent of essential hypertension. They further stated that there was no evidence of an increased mortality due to cardiovascular or cerebrovascular disease.

Although cadmium treatment administered by injection has been shown to induce prostate cancer and hypertension in rats (90, 93), several scientists have concluded that cadmium functions differently in rats than in humans (91); rat tissue is 30 times more sensitive to cadmium than is human tissue (92). Further, contrary to the relationship between cadmium administration and hypertension in rats, studies consistently have failed to correlate increased blood pressure with increased ingestion of cadmium in humans (94). In fact, a study of Japanese men and women who ingested high amounts of cadmium had lower blood pressure and a decreased incidence of cardiovascular disease than other Japanese whose diet was comparable but low:N cadmium (95).

As noted above, zinc has long been seen as an essential metal. The present invention is based upon the premise that cadmium also is an essential trace element. As defined herein, an essential element is one which when administered, reverses a reduction in a biological function (96). The reduction of function with cadmium deficiency in man is manifest with prostate cancer, hypertension and other diseases (97). Foods that are high in cadmium, such as leafy vegetables, cereals and grains, are associated with a lowered incidence of prostate cancer and hypertension.

Although not wishing to be bound by theory, it is believed that one biological role of cadmium is to regulate zinc homeostasis by decreasing zinc excretion in urine. It appears that cadmium acts as a regulator of zinc. When the level of cadmium is out of balance (i.e., if there is a cadmium deficiency), the levels of zinc cannot be regulated properly. In a healthy person, the concentration of zinc in the cells of tissues typically is high relative to that of cadmium; cadmium levels are lower relative to the levels of zinc in fluids. Thus, in a healthy person, the zinc:cadmium ratio is relatively high in cells and lower in fluids. Zinc is pumped into cells; cadmium is pumped out. Thus, looking at an organ, such as the kidneys or prostate, as a whole, when cadmium concentrations are high, zinc concentrations are high (98). If the person is cadmium deficient, however, cadmium does not get pumped out of the cell, however, and as a result, zinc is not pumped in. As a result, excess zinc in the fluids ultimately appears in the urine and is excreted. It is proposed that an underlying cause of certain diseases is a deficiency of cadmium leading to an increased urinary excretion of zinc and a secondary zinc deficiency.

It is believed that zinc and cadmium counterbalance one another in the body and that evaluating the movement of zinc and cadmium among red blood cells (erythrocytes), serum and cells, such as prostate cells in men and breast cells in women, provides an indication of relative health. The delivery of zinc from red blood cells to serum to cells of tissues is counterbalanced by the movement of cadmium from tissue cells to serum to red blood cells. A cadmium deficiency results in a slowdown of the zinc delivery system from red blood cells to serum to cells such as prostate cells.

There is evidence that serum zinc is regulated in the body. It is known that serum zinc in man is diurnal, with levels highest in the morning and lowest in the afternoon (99). Urinary excretion of cadmium is lowest in the morning and highest in the afternoon (100). When serum zinc decreases, urinary zinc excretion is decreased in a reflex fashion by a counter increased excretion of cadmium. This counter high cadmium urinary excretion with apparent decreased urinary zinc excretion in man is shown in the afternoon when the declining serum zinc stimulates an elevated urinary excretion of cadmium. If the body has an insufficient amount of cadmium, it is unable to counterbalance effectively urinary excretion of zinc, resulting in an increase in the amount of zinc excreted in the urine and a secondary zinc deficiency. It is theorized that a low cadmium diet causes a primary low level of cadmium in the body which is exaggerated by a high zinc diet which elevates the level of zinc in serum. When the elevated serum zinc level falls, it stimulates increased cadmium renal excretion which blocks excretion of renal zinc. This increased urinary excretion of cadmium results in a secondary cadmium deficiency. A cycle thus results, wherein a low cadmium diet causes a primary cadmium deficiency, and a high zinc diet causes an increased urinary excretion of cadmium which causes a secondary cadmium deficiency. The cadmium deficiency, in turn, prevents the renal retention of zinc, and the increased urine excretion of zinc results in a secondary zinc deficiency.

It further appears that a second biological role for cadmium is the blockage of calcium channels. Evidence indicates that cadmium decreases the influx of extracellular calcium into cells, thereby decreasing activation of these cells. Cadmium is a documented blocker of calcium channels (102). Stallions have a low cancer mortality rate relative to man (8% vs. 24%, respectively). Whereas prostate cancer is one of the most frequently diagnosed cancers in man, it has never been diagnosed in stallions. The serum cadmium of stallions is slightly elevated in relation to man (1.186 ng/ml vs. 0.924 ng/ml). Proportionally, serum calcium is higher in stallions versus man (115,949 ng/ml vs. 89,004 ng/ml). It is proposed that this elevated serum calcium in stallions is secondary to the blockage of calcium channels. As would be expected if the elevated serum calcium of stallions is secondary to a blockage of calcium channels, the observed intracellular red blood cell calcium is significantly lower in stallions than it is in man. Hypocalcemia in man is associated with some prostate cancers (103).

It is known that the highest concentration of zinc in a man's body is in his prostate gland (18). It also is known that the highest concentrations of prostaglandin E2 (PGE2) are in his seminal vesicles (15, 16, 17). In women, the highest concentration of PGE2 is in her breast tissue. A positive feedback occurs between PGE2 and zinc; PGE2 increases the absorption of zinc from the gut (19, 20) and zinc increases the PGE2 levels in tissues (21, 22). In contrast to zinc, cadmium decreases PGE2 levels (23, 24). Protease inhibitors also decrease PGE2, as secretory leukocyte protease inhibitors suppress the production of monocyte prostaglandin H synthase-2, PGE2 and matrix metalloproteinases (25). PGF2α has opposing physiologic actions to PGE2.

It now has been found that a deficiency of cadmium hinders the movement of cadmium from cells to serum to red blood cells, and, therefore, the counter-movement of zinc from red blood cells to serum to cells, leading to abnormal shifts in the levels of zinc and cadmium and, therefore, zinc-containing and PGE2-dependent matrix metalloproteinases, and that these fluctuations are associated with a number of diseases.

Thus, in accordance with one embodiment of the present invention, it now has been found that a person can be screened for an indication of or risk of developing a disease associated with unbalanced levels of cadmium in body fluids and tissues by measuring the level of cadmium, or the level of zinc, in a sample of his or her body fluid to determine whether the level is outside of normal, physiological levels. As used herein, an "unbalanced" or "fluctuating" level of cadmium means a level which is less than the minimum of the normal, physiological range. An unregulated or fluctuating level of zinc or calcium means a level which either exceeds the maximum, or is less than the minimum, of the normal, physiological range. For example, a person suffering from a cadmium deficiency has a level of cadmium in his red blood cells, in his urine and, if a man, in his seminal plasma, which is below the normal levels of cadmium in red blood cells or seminal plasma. Given the opposing interrelationship between cadmium and zinc in the body, such a person also typically will be found to have levels of zinc in his red blood cells and seminal plasma which exceed normal physiological levels. In contrast, a person with a cadmium deficiency has a relatively low amount of zinc and a relatively high amount of cadmium in tissues such as his prostate, for, as a result of the deficiency, there is less cadmium moving out of the prostate into the serum and less zinc migrating from the serum into the prostate.

The body fluid assayed can include serum or urine or, if the patient is a man, his seminal plasma. It is preferred to assay either urine or seminal plasma. Alternatively, a component of a body fluid, such as red blood cells (erythrocytes), can be assayed to determine the level of cadmium. Assaying the level of cadmium in red blood cells is a preferred method of determining a cadmium deficiency. Below normal levels of cadmium in red blood cells also is an indicator of the presence of, or risk of developing, certain diseases. As used herein, references to assaying or measuring cadmium levels in body fluids is intended to include measuring cadmium in a body fluid component such as red blood cells.

In accordance with this invention, the level of cadmium in a person's body fluid can be measured simply by taking a measure of the amount of cadmium in the selected body fluid. Thus, for example, a person can be screened for an indication of or risk of developing a disease associated with unbalanced levels of cadmium in body fluids and tissues by measuring the level of cadmium in a sample of his or her red blood cells, urine or, if the person is male, in his seminal fluid.

A person is considered to be at risk for developing, or to be in the preliminary stages of developing, a disease, if the level of cadmium in his or her body fluid is more that about 15%, and preferably more than about 20%, below normal levels, or if the level of zinc in his or her body fluid is more than about 15%, and preferably more than about 20% above normal levels. For example, low normal levels of cadmium in red blood cells of healthy men typically are in the range of about 1.2–1.3 ng/g. Men whose levels are less than about 1.0 ng/g have a cadmium deficiency. The lower limits of normal levels of cadmium in urine typically are about 0.26–0.28 ng/ml; a level less than about 0.23 ng/ml is an indication of cadmium deficiency. Low normal levels of cadmium in seminal plasma are about 3.2–3.4 ng/ml; a level of less than about 2.8 ng/ml is considered deficient.

A preferred way of determining whether someone has a cadmium deficiency is to measure not simply the concentration of cadmium in a body fluid or body fluid component, but to also measure the concentration of cadmium in a second body fluid and then to determine the movement of cadmium from one to the other. For example, one can measure the movement of cadmium between serum and red blood cells by using the following equation:

Cd conc. in red blood cells/(Cd conc. in red blood cells+Cd conc. in serum)

In healthy men whose levels of cadmium are at or near the low end of the healthy range, this ratio typically is within the range of about 0.51–0.53 (not corrected for hemoglobin); a level of less than about 0.44 is indicative of a cadmium deficiency.

Similarly, a cadmium deficiency can be determined by measuring the concentration of cadmium in the person's serum and in his or her urine, and then determine the movement of cadmium between serum and urine by use of the following equation:

Cd conc. in urine/(Cd conc. in urine+Cd conc. in serum)

In healthy men whose levels of cadmium are at or near the low end of the normal range, this ratio typically is within the range of about 0.20–0.21 (not adjusted for creatinine); a level of less than about 0.17 is indicative of a cadmium deficiency.

If the level of cadmium in samples of a person's body fluid is at least about 15% below normal levels (and/or the level of zinc in the samples is at least about 15% above normal levels), one or more follow-up examinations and/or tests in accordance with conventional medical practice can be carried out to determine if the person is already in the early stages of a disease associated with a cadmium deficiency. If the person has no other indications of disease, one or more bioavailable cadmium salt(s) can be administered to balance his or her level of cadmium and also, therefore, regulate zinc to delay or prevent the onset of such a disease. If other indications of the presence of a disease are found, cadmium salt administration can be combined with one or more conventional therapies for the disease in question.

The administration of the cadmium salt(s) will decrease elevated ratios of PGE2:PGF2α and regulate zinc:cadmium in the recipient's body. As used herein, "balancing" or "regulating" means to minimize or eliminate abnormal deviations in the level of zinc or cadmium in body fluids. Thus, it means to minimize or eliminate abnormally high levels of, or abnormal shifts or fluctuations in the levels of, zinc (and, therefore, zinc-containing and PGE2-dependent matrix metalloproteinases) in body fluids or to increase below normal levels of, or abnormal shifts or fluctuations of, cadmium to approximate normal physiological levels. Diseases associated with unbalanced levels of cadmium and/or unregulated levels of zinc or increased levels of zinc-containing or PGE2-dependent matrix metalloproteinases in body fluids include diabetes, osteoporosis, Alzheimer's disease, hypertension and cancers, such as prostate cancer, colon cancer and breast cancer.

To balance the systemic cadmium levels and to regulate the systemic zinc levels in a person who has been found to have unbalanced levels of cadmium and/or unregulated levels of zinc in his or her body fluids, cadmium salts are administered. The cadmium salts regulate the PGE2:PGF2α and zinc:cadmium ratios in the patient's blood, other body fluids and tissues. In turn, as matrix metalloproteinases are regulated by zinc and PGE2, the systemic decrease in zinc and PGE2 levels resulting from the cadmium administration inhibits the PGE2-dependent matrix metalloproteinases. By regulating the level of matrix metalloproteinases, zinc, and cadmium, the onset of diseases which have been shown to be associated with unregulated levels of zinc in body fluids and tissues and matrix metalloproteinases in the body can be prevented or delayed, and the progression of the disease in one who has already contracted it can be halted or slowed.

Cadmium salts can be administered as an effective therapy for persons suffering from diseases associated with unregulated levels of zinc (and, therefore, high levels of zinc-containing and PGE2-dependent matrix metalloproteinases) and/or unbalanced levels of cadmium in body fluids and/or high calcium channel influx. Cadmium administration serves to decrease elevated ratios of PGE2:PGF2α and to regulate ratios of zinc:cadmium in the body fluids of a human. Cadmium administration also serves to block calcium channels and, therefore, to regulate the influx of extracellular calcium into red blood cells and other cells. As used herein, "treatment" includes halting or slowing the progress of a disease. Diseases which are influenced by zinc, cadmium and matrix metalloproteinase levels include diabetes, osteoporosis, Alzheimer's disease and hypertension and cancers, such as prostate, colon and breast cancer. Diseases which are influenced by high amounts of calcium in red blood cells include hypertension and certain cancers, such as prostate cancer.

For example, as noted above, high levels of matrix metalloproteinases have been shown to be associated with the metastasis of at least certain types of cancer cells. Accordingly, bioavailable cadmium salts can be administered to effect a treatment for, or to prevent or delay the onset of, certain types of cancer, such as prostate cancer, colon cancer or breast cancer. By regulating the concentration of zinc and cadmium in body fluids the concentration of zinc-containing and PGE2-dependent matrix metalloproteinases can be decreased and stabilized.

It also has been found that significant fluctuations of normal zinc concentrations are associated with the onset and progression of other diseases. For example, diabetes patients have been shown to have approximately double the normal amounts of zinc in their urine and about 15–20% below normal levels of zinc in their blood (77, 78). It also has been found that osteoporosis patients often have increased urinary zinc excretion (101). In addition, cadmium levels have been found to be abnormally low in the cerebrospinal fluid (CSF) of Alzheimer's patients. The administration of a physiologically and bioavailable cadmium salt can minimize these fluctuations and regulate the levels of zinc excreted in urine. Although not wishing to be bound by theory, it appears, as noted above, that cadmium competes with zinc in pathways in the body. Thus, in the case of a diabetic patient who has large amounts of zinc in his urine, it is postulated that the administration of cadmium leads to a competition between the processing of cadmium and the processing of zinc in the patient's kidneys, resulting in less zinc being excreted in the urine and an accompanying adjustment in systemic zinc levels to more normal levels. In patients with elevated systemic levels of zinc, the administration of cadmium serves to lower the ratio of zinc to cadmium.

Cadmium salts are administered to a patient so as to regulate the PGE2:PGF2α and zinc:cadmium ratios in the patient's blood and other body fluids and body fluid components and tissues, thereby regulating the patient's systemic levels of zinc, cadmium and PGE2. The cadmium salts are administered in a series of daily doses in effective amounts.

Cadmium salt(s) and other agents which optionally can be administered in combination with them, as discussed in detail below, can be administered orally, parenterally or by inhalation at a dose level of about 0.025 to about 2 mg/day. Oral administration, such as by capsules, tablets, suspensions or solutions, is preferred. Cadmium salt(s) conveniently are administered in the form of tablets. The cadmium salt(s) can be mixed with one or more lubricants, such as stearic acid or magnesium stearate, flavor ameliorating agents, disintegrating elements, including potato starch and alginic acid, binders, such as gelatin and corn starch, and/or tablet bases, such as lactose, corn starch and sucrose, and then pressed into tablets. Alternatively, the cadmium salt(s) can be given in the form of capsules, prepared by mixing the salt(s) with a pharmaceutically acceptable excipient and then filling gelatin capsules with the mixture in accordance with conventional procedures. If administered orally, the cadmium salt typically is administered at a dose of about 0.5 mg to about 2 mg per day, preferably about 0.8 to about 1.2 mg per day, and most preferably about 1 mg per day.

As an alternative to oral administration cadmium salt(s) can be administered parenterally, provided in injectable doses of a solution or suspension in a physiologically acceptable diluent with a pharmaceutical carrier. The carrier can comprise water or an oil and also optionally can comprise a surfactant or other pharmaceutically acceptable adjuvant. If administered parenterally, the cadmium salt typically is administered at a dose of about 0.025 mg to about 0.1 mg per day, preferably about 0.04 mg to about 0.06 mg per day.

As a further alternative, the cadmium salt(s) can be administered by inhalation. The salt(s) are provided in an aerosol spray and administered via an inhaler. If administered by inhalation, doses typically are within the range of about 0.05 to about 0.2 mg per day, preferably about 0.08 to about 0.12 mg per day, and most preferably about 0.1 mg per day.

For all avenues of administration, the doses useful in treating a disease are comparable to those to be used for preventing the disease.

Suitable salts are bioavailable cadmium salts. Such salts include the sulfate, nitrate, chloride and acetate salts. A single salt can be administered or a combination of salts can be used.

Optionally, the one or more cadmium salts can be administered in combination with at least one further therapeutic agent. In one embodiment of the invention, the cadmium salts are administered in combination with at least one estrogenic compound. This combined administration of cadmium salt and estrogen can be beneficial in the treatment or prevention of diseases associated with unregulated levels of zinc, and is of particular benefit for the prevention or treatment of prostate cancer. The estrogenic compound(s) act synergistically with the cadmium salt(s) to directly prohibit PGE2 production in semen, blood and other bodily fluids. A single estrogen can be administered or a mixture of estrogens can be used. Suitable conjugated estrogenic compounds include those found in commercially available estrogen preparations, such as Premarin®, or a plant-based or synthetic conjugated estrogen preparation, such as Cenestin®, Estrace, Estraderm or OrthoDienestrol. The principal estrogen in Premarin® is sodium estrone sulfate. The estrogenic compound(s) can be administered at a daily dose of about 0.1 mg to about 0.5 mg, preferably about 0.3 mg per day. The actual amount of estrogen(s) used will depend upon the particular estrogen selected and its relative potency.

Another embodiment of the present invention comprises the administration of cadmium salt(s) in combination with one or more protease inhibitors to synergistically decrease levels of PGE2 concentration in blood, and other body fluids. Proteases play pivotal roles in sperm function (58, 59, 60, 61, 62) and cancer cell metastasis (64, 65, 66, 67, 68, 69, 70, 71, 72, 73). The administration of protease inhibitors can block these proteases and thereby decrease sperm and cancer cell function. A number of protease inhibitors are known and have been proposed or used as therapeutic agents. For example, several studies have described the negative effects of protease inhibitors on fertility. Protease inhibitors can decrease the penetration rate of human sperm into oocytes (58) and, in seminal plasma, can act as decapacitation factors (61, 62).

In addition, a number of patents, such as U.S. Pat. Nos. 5,830,888, 5,708,004, 5,602,175, and 5,527,829, describe the administration of protease inhibitors as anti-HIV therapeutics. A number of protease inhibitors (e.g., invirase, ritonavir, indinavir sulfate, and nelfinavir mesylate) have been found to prevent reverse transcription of HIV (63).

U.S. Pat. No. 4,906,457 reports the use of protease inhibitors for cancer protection. A serine protease inhibitor, FOY-305, inhibits the invasion of tumor cells through interference with the u-PA activity of tumor cells (64). Selective protease inhibitors at 10 nM concentration in the culture medium inhibit the migration of tumor cells in a Matrigel assay (65). Dietary phytochemicals have protease inhibitory activity, and also inhibit cancer (66). The recognized relationship between protease inhibitors and cancer is demonstrated by a second conference on "Proteases and Protease Inhibitors in Cancer" that was held in 1998 (68).

Useful protease inhibitors in accordance with the present invention include those in the patents cited above, the teachings of which are incorporated herein by reference, and those found in stallion urine. U.S. Pat. No. 3,912,704, incorporated herein by reference, describes protease inhibitors from stallion urine. The molecular weight of the protease inhibitors from stallion urine are 26,000–28,000 by gel filtration, 17,000 by polyacrylamide gel electrophoresis, and 20,400 by ultracentrifuge. Other suitable protease inhibitors include those described in the patents cited above, including indinavir sulfate, commercially available as Crixivan® (Merck); ritonavir, commercially available as Norvir® (Abbott); invirase, commercially available under the name Saquinavir® (Immunet); and nelfinavir mesylate, commercially available as Viracept® (Agouron).

When one or more protease inhibitors is administered in combination with the cadmium salt(s), the dose of the protease inhibitor varies depending upon the particular inhibitor or inhibitors chosen, but typically is in the range of from about 600 mg to about 2400 mg per day, depending upon the strength of the particular compound(s) of interest. For example, a preferred daily dose of indinavir sulfate typically is about 800 mg orally every eight hours, a preferred daily dose of ritonavir is within the range of about 300 mg to about 600 mg twice a day, a preferred daily dose of invirase is about 200 mg three times a day and a preferred daily dose of nelfinavir mesylate is about 750 mg three times per day. If desired, the protease inhibitor can be administered in combination with an estrogenic compound in addition to a cadmium salt.

In accordance with this invention, for purposes of the prevention or treatment of prostate cancer, breast cancer or colon cancer, the cadmium salts are administered in a series of doses in an amount sufficient to prevent or inhibit the formation, growth, division, or metastasis of cancer cells. For purposes of the prevention or treatment of diabetes, osteoporosis, hypertension or Alzheimer's disease, the cadmium salt(s) are administered in a series of doses in an amount sufficient to regulate fluctuations in the levels of zinc and the zinc-containing and PGE2-dependent matrix metalloproteinases in the patient's body fluids which have been found to be associated with the disease.

The examples set forth below are intended to further illustrate the present invention and are not intended to be limiting.

EXAMPLES

As shown in Example 1, 1) PGE2, PGF2α, and zinc occur at higher concentrations in man's than in stallion's semen and cadmium occurs at a lower concentration in man's than in stallion's semen, and 2) the ratio of PGE2:PGF2α is higher in man's semen than in stallion's semen and the ratio of zinc:cadmium is higher in man's semen than in stallion's semen.

As shown in Example 2, observed sperm motility in 5 stallions was higher when the zinc:cadmium ratio was higher.

Example 3 provides the results of assays of cadmium, zinc and calcium levels in body fluids and the movement of cadmium and zinc from one body fluid to another.

Example 1

Evaluation of Semen Samples

SEMEN COLLECTION: Sperm-rich fractions of semen were collected from 8, healthy Morgan stallions aged 2–15 years old. The collected semen was immediately diluted 1:1 with 20 mg/ml aspirin in ultra-pure water and transported on ice to the laboratory. The stallion semen samples were frozen until analysis. Just prior to assay, samples were thawed and purified by centrifugation and then assayed for PGE2, PGF2, zinc and cadmium.

Nine semen samples were collected from a healthy, 46-year-old man over a 45-day period which began on November 13. The first five of the samples were collected over the first 27 days and were collected as controls. Then, over an 18 day period, the man was administered 350 cc of stallion urine twice daily. The urine previously had been harvested from three Arabian stallions and frozen. The remaining four samples of the man's semen were collected during this 18 day period. Each semen sample was purified by centrifugation and the top 1 ml was aspirated and frozen. The remaining semen also was frozen, then, just prior to assay, the samples were thawed and purified by centrifugation and then assayed for PGE2, PGF2, zinc and cadmium.

Centrifugation of both stallion and man's semen samples consisted of a primary centrifugation to remove cells and debris (at 500×g for 10 minutes at 4° C.) and then a secondary centrifugation to remove large proteins (at 80,000×g for 90 minutes at 4° C.). The stallion semen and all human semen samples were assayed for PGE2 and PGF2α by radioimmunoassay or enzyme immunoassay.

PGE2, PGF2α, Zinc, and Cadmium Assays:

Concentrations of PGE2 in human semen were quantified using acetylcholinesterase competitive enzyme immunoassay kits (Cayman Chemical Company, Ann Arbor, Mich.). The assay uses 96-well microtiter plates, with goat anti-mouse polyclonal antibody previously bound to each well, and pure acetylcholinesterase from the electric eel (*Electrophorus electricus*) that is covalently coupled to PGE2 as the enzymatic tracer. The human semen PGE2 assays were performed according to manufacturer's directions. Briefly, semen samples were thawed and further purified by chromatography (using Waters Sep-Pak cartridges (Millipore Corp. Milford, Mass.)). Purified samples then were reconstituted with 450 µl of EIA buffer, and diluted to final concentrations of 1/10,000 to 1/100,000. Fifty microliters of each sample (from each dilution) were added to each well, followed by 50 µl of PGE2 acetylcholinesterase tracer and 50 µl of PGE2 monoclonal, anti-PGE2 antibody per well. Each dilution from each of the 9 semen samples was assayed in duplicate. Plates were incubated for 18 hours at 4° C., were then rinsed thoroughly with wash buffer, and 200 µl of Ellman's reagent was added to each well. Development occurred after 60–90 minutes in darkness. Plates were read at 405–420 nm with a spectrophotometer. Simultaneously incubated were wells with 50 µl of PGE2 standard with 50 µl of tracer and 50 µl of anti-PGE2 antibody. Nonspecific binding was determined by incubating 100 µl of EIA buffer and 50 µl of tracer, and maximum binding ($B_0$) was determined by incubating 50 µl EIA buffer, 50 µl of tracer, and 50 µl of anti-PGE2 antibody.

Concentrations of PGF2α in stallion semen samples and in human semen samples were quantified by radioimmunoassay, with [5, 6, 8, 9, 11, 12, 14, 15(n)-$^3$H]-PGF2α (sa 200 Ci/mmol; New England Nuclear, Boston, Mass.), rabbit anti-PGF2α antibody (1:20,000 final dilution; supplied by D. H. Dubois & F. W. Bazer) and Lutalyse (Upjohn Co., Kalamazoo, Mich.) for standards (94). Briefly, just prior to assaying, diluted, previously frozen stallion semen samples were thawed and purified by centrifugation (as described above). Human semen samples (which had been centrifuged prior to freezing) were thawed and diluted 1:1 with 20 mg/ml aspirin in ultra-pure water. Assay tubes received 25 µl of each sample plus 100 µl of [3H]-PGF2α, 200 µl of assay buffer (50 mM Tris HCl and 0.01% $NaN_3$ at pH 7.5, 4° C.), and 100 µl of anti-PGF2α. Tubes were incubated at room temperature for 30 minutes and then 18–24 hr at 4° C. Free PGF2α was then separated from antibody-bound PGF2α by addition of 0.5 ml of 0.25% Norit A charcoal and 0.025% dextran (in assay buffer) for 4 min at 4° C., followed by centrifugation for 10 min at 1,800×g and at 4° C. The amount of antibody-bound [3H]-PGF2α in 0.5 ml of supernatant was determined by liquid scintillation spectrometry. A log-logit regression program was used to calculate concentrations of PGF2α (95). Assay sensitivity is 2.5 pg/tube ($p<0.01$). Cross-reactivity of the antisera is 63.0% for PGF1α, 0.3% for PGE2, and <0.1% each for 6-keto-PGF1α, PGFM and arachidonic acid (94).

After dilution, freezing, thawing, and purification of the stallion semen samples, concentrations of PGE2 were quantified similarly using the same radioimmunoassay techniques as for PGF2α, except with [5, 6, 8, 11, 12, 14, 15(n)-$^3$H]-PGE2 (sa 200 Ci/mmol; New England Nuclear, Boston, Mass.), rabbit anti-PGE2 (1:20,000 final dilution; supplied by D. H. Dubois & F. W. Bazer) and PGE2 (Sigma Chemical Co., St. Louis, Mo.) for standards.

STATISTICS: The mean concentrations of PGE2, PGF2α, zinc, and cadmium, and the mean ratios of PGE2:PGF2α and zinc:cadmium were contrasted by the Student T test between stallion semen and human semen (control samples) and among human samples.

Results

Tables 1 and 2 show the results of experiment 1. In experiment 1, PGE2 is 4,556 (368,570.0/80.9) times greater ($p<0.01$) in concentration (ng/ml) in man's than in stallion semen. PGF2α is 116 (231.6/2.0) times greater ($p<0.01$) in concentration (ng/ml) in man's than in stallion semen. The PGE2:PGF2α ratio is 1597:1 (368,570.0/231.6) in man's semen, and 39:1 (80.9/2.0) in stallion semen. Therefore, the PGE2:PGF2α ratio is 41 (1597/39) times greater ($p<0.01$) in man's than in stallion semen.

Also, from experiment 1, zinc is 76 (68,640.0/897.3) times greater ($p<0.05$) in concentration (ng/ml) in man's than in stallion semen. In contrast, cadmium was below detectable levels (<0.2 ng/ml) in all of the man's control semen samples, but was detected (1.6 to 11.4 ng/ml) in 5 of the 8 stallion semen samples. Therefore, cadmium is at least 13 (2.6/0.2 ng/ml) times greater ($p<0.01$) in concentration (ng/ml) in stallion than in man's semen. The zinc:cadmium ratio is 301 (343,200/1,139) times greater ($p<0.05$) in man's than in stallion semen.

TABLE 1

Prostaglandin E2 (PGE2), prostaglandin F2 alpha (PGF2α), zinc, and cadmium concentrations (mg/ml) in stallion semen.

| Sample No. | PGE2 | PGF2α | (ratio) | Zinc | Cd. | (ratio) |
|---|---|---|---|---|---|---|
| 1 | 94.2 | 1.8 | (52:1) | 1,624.0 | <0.4 | (4,060:1) |
| 2 | 72.5 | 1.6 | (45:1) | 920.0 | 11.4 | (81:1) |
| 3 | 80.7 | 3.0 | (27:1) | 1,048.0 | 2.0 | (524:1) |
| 4 | 63.4 | 2.7 | (23:1) | 596.0 | 1.6 | (373:1) |
| 5 | 214.7 | 3.5 | (61:1) | 1,302.0 | 3.2 | (407:1) |
| 6 | 51.5 | 1.7 | (30:1) | 296.0 | 1.6 | (185:1) |
| 7 | 48.6 | 0.9 | (54:1) | 484.0 | <0.4 | (1,210:1) |
| 8 | 21.6 | 1.0 | (22:1) | 908.0 | <0.4 | (2,270:1) |
| Average | 80.9 | 2.0 | (39:1) | 897.3 | 2.6 | (1,139:1) |

Conclusions

The concentration of PGE2 is 4,556 times greater and the concentration of PGF2α is 116 times greater in man's than in stallion's semen. Also, the PGE2:PGF2α ratio is 41 times greater in man's than in stallion's semen. Therefore, the stallion has regulatory mechanisms that maintain a 4,000 fold lower concentration of PGE2 and a 100 fold lower concentration of PGF2α than in the semen of man. Because the PGF2α concentration is only 100 fold lower in stallions than in man, the ratio of PGE2:PGF2α is 41 times lower in stallion's semen than in man's semen.

The concentration of zinc is 76 times greater and the concentration of cadmium is at least 13 times lower in man's than in stallion's semen. Also, the zinc:cadmium ratio is at least 301 times greater in man's than in stallion's semen. Therefore, the stallion has regulatory mechanisms that maintain a 76 fold lower concentration of zinc and a 13 fold higher concentration of cadmium than in the semen of man.

Example 2

Material and Methods

Two ejaculates were collected from each of five Quarter Horse stallions. Each ejaculate was evaluated for gel-free volume, sperm concentration, and sperm motility. In addition, each sample was chemically analyzed for the concentration cadmium.

TABLE 2

Concentration of cadmium and sperm motility in paired ejaculates from five Quarter Horse stallions.

| Stallion | Ejaculate Number | Cadmium (µg/ml) | Sperm Motility |
|---|---|---|---|
| A | 2 | 0.2 | 70 |
|   | 1 | 1.0 | 60 |
| D | 1 | 0.3 | 85 |
|   | 2 | 0.4 | 75 |
| G | 2 | 0.3 | 80 |
|   | 1 | 1.0 | 67.5 |
| H | 1 | 0.2 | 85 |
|   | 2 | 1.4 | 80 |
| I | 1 | 0.5 | 82.5 |
|   | 2 | 0.6 | 75 |

Results

In all five stallions, when the concentration of cadmium increased, the sperm motility decreased. Motility of sperm correlates to sperm viability and fertility and these data show that the sperm motility is higher in semen from paired semen samples when the naturally occurring concentration of cadmium is lower in the semen. Sperm viability is an indicator of the proliferation environment of the stallion's prostate gland. Thus, the higher cadmium values from semen decreases the proliferation (metastasis) of prostate cells and replication of viruses within the prostate environment. This test supports the thesis that elevating the cadmium concentration in man's prostate gland to mimic that of the stallion's relatively high cadmium concentration in his prostate gland decreases man's incidence of prostate cancer and other diseases.

Example 3

Experiment A

Seven healthy, non-smoking men ages 30–52 fasted from 6:00 p.m. of one evening until 8:00 a.m. the next day, then each had a standard breakfast consisting of a poppy seed muffin and a half liter of orange juice. Blood and urine collection began at 6:00 a.m. and ended at 8:00 p.m. Every hour one syringe of blood was drawn from a catheter for the purpose of obtaining blood serum. During the hours of 8:00 a.m., 1:00 p.m. and 7:00 p.m. blood was drawn every 15 minutes. The men consumed a prepared lunch of chicken salad between the hours of 12 noon and 2:00 p.m. Two liters of bottled water were provided to each man to drink freely throughout the day. Urine samples were collected at two hour intervals. Eight urine samples and twenty four blood samples were collected for each man.

Experiment B

Fifty five men were recruited as volunteers for the collection of blood. Two samples were collected per man for the purpose of obtaining blood serum and erythrocytes. The men were non-smokers, healthy and ranged in age from 19 to 61 years with a mean age of 38 years.

Fifty five mixed breed light horse stallions were recruited as comparative subjects to the men. The stallions were healthy and ranged in age from 2 to 31 years. Two blood samples were obtained from each stallion.

Experiment C

One hundred and two men participated in a one day study involving urine and blood collection. Participants were selected based on their PSA levels. Fifty five of the men had a PSA level of less than 2.0 ng/ml and were identified as having a low PSA. Forty seven men comprised the second group and had PSA levels of 2.0 ng/ml or higher. The men fasted from 6:00 p.m. the evening prior to sampling until breakfast at 8:00 a.m. the day of collection. Each man had a standard breakfast of a poppy seed muffin and a half liter of orange juice. Blood and urine collection began at 6:00 p.m. and ended at 8:00 p.m. Two syringes of blood were drawn from each man prior to 12 noon for the purpose of obtaining blood serum and erythrocytes. The men consumed a prepared lunch of a large chicken salad between the hours of noon and 2:00 p.m. Two liters of bottled water were provided for each man to drink freely throughout the day. Each man was given a urine collection kit and instructions to obtain his urine sample during the day. Urine was collected every other hour for a total of eight samples per man.

Experiment 4

Three healthy men with low PSA levels (below 2 ng/ml) volunteered for weekly blood and urine collection while a serial treatment of zinc, zinc with cadmium, and cadmium was administered. Treatment was given daily over a nine week period, followed by three weeks of continued sampling with no treatment. The zinc was administered in the form of zinc sulfate ($ZnSO_4$) at a daily dosage of 75 mg. The cadmium was administered in the form of cadmium sulfate ($CdSO_4$) at a daily dosage of 1 mg. Blood and urine were collected one day prior to the beginning of treatment for purposes of establishing a baseline level of chemicals in the blood and urine. Zinc salt administration began on the second day of the study and was administered each morning. On day 15, the cadmium salt administration was begun in the evening, with continued zinc salt administration continuing in the morning. Zinc administration was discontinued on day 43; cadmium administration continued through day 57. On days 58–78 of the study, neither zinc nor cadmium was administered, but blood and urine samples continued to be collected. Blood and urine were collected one day each week (days 1, 8, 15, etc.) for a total of 12 collection days over an 11 week period.

The men food fasted for 24 hours each collection day, beginning at 6:00 p.m. the prior evening and continuing until 6:00 p.m. the evening of the collection day. Two liters of bottled water were provided to each man to drink freely throughout the day. Two syringes of blood were drawn from each man prior to 12 noon each collection day for the purposes of obtaining blood serum and erythrocytes. Each man was given a urine collection kit and instructions to obtain his urine sample during the day. Urine was collected every two hours beginning at 6:00 a.m. and ending at 6:00 p.m., totaling seven samples per man. Complete urinalysis, comprehensive metabolic, urine protein, and hemogram tests were performed on samples.

Blood Collection

Erythrocytes and blood serum were collected in a similar fashion for men and stallions in all experiments. Erythrocytes were not collected in Experiment A. A phlebotomist drew blood from the men. Venipuncture procedures were followed to obtain blood from the stallions. All blood samples were collected in two 9 ml heavy metal free syringes (Monovette, Sarstadt, Inc., Newton, N.C.). One syringe contained 250 µl of EDTA and was used to obtain erythrocytes. Immediately after collection, the EDTA tube was mixed gently and then centrifuged at 800 G for 15 minutes. The plasma then was removed along with a layer of white blood cells. The erythrocytes were washed in the following manner. Three ml. of Tris (Tris hydroxymethyl aminomethane hydrochloride) buffered saline (pH 7.0) were added to the erythrocytes and the combination was mixed gently for 1 minute. The tube was centrifuged at 800 G for 15 minutes. The supernatant subsequently was removed and the process was repeated once more. After washing, the erythrocytes were re-suspended in a volume of saline equal to the original volume of blood.

The second syringe contained no EDTA and was used to collect blood serum. After collection, the whole blood samples were stored at room temperature (21° C.) until the blood clot contracted. Tubes then were centrifuged at 800 G for 15 minutes. The serum subsequently was removed with a disposable polypropylene transfer pipette and placed into 1.7 ml micro centrifuge tubes (Gene Mate Dist. by ISC Bio Express, Kaysville, Utah). All processed blood samples were stored in a −80° C. freezer until analyzed.

Urine Collection

Urine samples from the men were collected in heavy metal free polypropylene cups which had been rinsed with Radiacwash (Biodex Medical systems, Shirley, N.Y.) to removed heavy metal and ion residue. The urine was kept refrigerated following collection. At the end of the collection period, the samples were retrieved and processed. The urine from each cup was transferred into 30 ml polypropylene bottles previously rinsed with Radiacwash and stored in a −80° C. freezer.

To collect urine from the stallions, an open end of a plastic fingerless sleeve was attached to a 5½ inch plastic embroidery hoop. The hoop was secured over the sheath of the stallion with a 4 inch ace bandage wrapped around the lower abdomen. Each time a horse urinated, the collection device was removed and replaced with a new one. Immediately following each collection the urine sample was transferred into 60 ml polypropylene bottles that had been washed with Radiacwash. The samples were stored in a −80° C. freezer.

PSA

One ml of blood serum was used for PSA assays. Total and free PSA were analyzed using Hybritech® PSA from Beckman Coulter. Results were reported in ng PSA/ml of serum.

Heavy Metal Analysis

Serum and urine calcium, zinc and cadmium were reported in ng/ml and µg/ml. All samples were stored in a −80° C. freezer. Samples were digested using an AIM-500 DriBlock programmable Digester with UTAK Normal Range Control and Chem TRAK Plus Level 1. Heavy metal analysis was performed using a Perkin Elmer Optima 3300 DV ICPAES.

Results

As shown in Table 3, serum calcium was less in seven men than in the seven stallions (Experiment A). The lower calcium in men than stallions was interpreted to result from greater penetration of calcium into cells with expected higher cell activity. Lower serum calcium and greater erythrocyte calcium was detected in 55 men than in 55 stallions (Experiment B) (Table 4). Blockage of calcium penetration into erythrocytes (defined as serum calcium/erythrocyte calcium) was four times lower for the men than for the stallions.

TABLE 3

Calcium, Zinc, and Cadmium (ng/ml) in the Serum and Urine of 7 Men and 7 Stallions (Experiment A)

| | | Men | Stallions | (p value) |
|---|---|---|---|---|
| Calcium | Serum | 89,014.998 | 116,076.012 | (<0.001) |
| | Urine | 92,658.323 | 1,515,423.775 | (0.001) |
| | Urine/Serum | 1.035 | 13.094 | (0.001) |
| | Ur/(Ur + Ser) | 0.444 | 0.873 | (0.001) |
| | Serum/Urine | 1.661 | 0.178 | (0.001) |
| | Ser/(Ser + Ur) | 0.556 | 0.127 | (0.001) |
| Zinc | Serum | 842.374 | 455.698 | (<0.001) |
| | Urine | 600.454 | 133.628 | (0.001) |
| | Urine/Serum | 0.743 | 0.284 | (0.026) |
| | Ur/(Ur + Ser) | 0.386 | 0.207 | (0.026) |
| | Serum/Urine | 1.919 | 5.218 | (0.26) |
| | Ser/(Ser + Ur) | 0.614 | 0.793 | (0.026) |
| Cadmium | Serum | 0.927 | 1.214 | (0.251) |
| | Urine | 2.167 | 0.201 | (<0.001) |
| | Urine/Serum | 2.527 | 0.185 | (<0.001) |
| | Ur/(Ur + Ser) | 0.682 | 0.152 | (<0.001) |
| | Serum/Urine | 0.514 | 7.523 | (<0.001) |
| | Ser/(Ser + Ur) | 0.318 | 0.848 | (<0.001) |

TABLE 4

Calcium, Zinc, and Cadmium (ng/ml) in the Serum and Erythrocytes of 55 Men and 55 Stallions (Experiment B)

| | | Men | Stallions | (p value) |
|---|---|---|---|---|
| Calcium | Serum | 92,478.586 | 136,572.625 | (<0.001) |
| | Erythrocytes | 1,429.573 | 576.456 | (<0.001) |
| | Erythrocytes/Serum | 0.016 | 0.004 | (<0.001) |
| | Eryth/(Eryth + Ser) | 0.015 | 0.004 | (<0.001) |
| | Serum/Erythrocytes | 91.450 | 379.206 | (<0.001) |
| | Ser/(Ser + Eryth) | 0.985 | 0.996 | (<0.001) |
| Zinc | Serum | 997.354 | 653.566 | (<0.001) |
| | Erythrocytes | 3,446.093 | 1,473.593 | (<0.001) |
| | Erythrocytes/Serum | 3.586 | 2.314 | (<0.001) |
| | Eryth/(Eryth + Ser) | 0.756 | 0.675 | (<0.001) |
| | Serum/Erythrocytes | 0.361 | 0.515 | (<0.001) |
| | Ser/(Ser + Eryth) | 0.244 | 0.325 | (<0.001) |
| Cadmium | Serum | 0.942 | 1.040 | (<0.001) |
| | Erythrocytes | 1.311 | 0.608 | (0.003) |

TABLE 4-continued

Calcium, Zinc, and Cadmium (ng/ml) in the Serum and
Erythrocytes of 55 Men and 55 Stallions (Experiment B)

|  | Men | Stallions | (p value) |
|---|---|---|---|
| Erythrocytes/Serum | 1.438 | 0.591 | (0.001) |
| Eryth/(Eryth + Ser) | 0.448 | 0.365 | (0.009) |
| Serum/Erythrocytes | 1.970 | 1.824 | (0.300) |
| Ser/(Ser + Eryth) | 0.552 | 0.635 | (0.009) |

PSA measures prostate cell activity and calcium penetration into cells in men greater than 50 years of age, men with high PSA (defined as 2.0 ng/ml or greater) were expected to have low serum calcium, high erythrocyte calcium and low blockage of calcium penetration into erythrocyte when contrasted with men with PSA of less than 2.0 ng/ml. As predicted, serum calcium was less, erythrocyte calcium was greater and blockage of calcium penetration into erythrocytes was less for men with high PSA than men with low PSA (Table 5). Calcium was observed to have lower extracellular concentrations (serum), higher intracellular concentrations (erythrocytes) and lower blockage to erythrocyte penetration in individuals with high proliferation (i.e., men vs. stallions(Experiments A and B) and men with high PSA vs. men with low PSA (Experiment C)).

TABLE 5

Calcium, Zinc, and Cadmium (ng/ml) in the Serum,
Erythrocytes, and Urine of 55 High PSA Men (>2.0 ng/ml)
and 47 Low PSA Men (<2.0 ng/ml) (Experiment C)

|  |  | High PSA Men | Low PSA Men | (p value) |
|---|---|---|---|---|
| Calcium | Serum | 94,475.839 | 97,942.122 | (<0.001) |
|  | Erythrocytes | 997.187 | 764.627 | (<0.001) |
|  | Urine | 26,839.109 | 29,605.251 | (0.248) |
|  | Erythrocytes/Serum | 0.011 | 0.008 | (<0.001) |
|  | Eryth/(Eryth + Ser) | 0.010 | 0.008 | (<0.001) |
|  | Serum/Erythrocytes | 119.858 | 551.226 | (<0.001) |
|  | Ser/(Ser + Eryth) | 0.990 | 0.992 | (<0.001) |
|  | Urine/Serum | 0.283 | 0.302 | (0.386) |
|  | Ur/(Ur + Ser) | 0.197 | 0.212 | (0.370) |
|  | Serum/Urine | 9.184 | 5.608 | (0.204) |
|  | Ser/(Ser + Ur) | 0.803 | 0.788 | (0.370) |
| Zinc | Serum | 901.900 | 1,025.993 | (<0.001) |
|  | Erythrocytes | 2,025.308 | 1,753,628 | (0.166) |
|  | Urine | 182.817 | 190.157 | (0.386) |
|  | Erythrocytes/Serum | 2.253 | 1.740 | (0.014) |
|  | Eryth/(Eryth + Ser) | 0.651 | 0.596 | (0.016) |
|  | Serum/Erythrocytes | 0.663 | 0.772 | (0.016) |
|  | Ser/(Ser + Eryth) | 0.349 | 0.404 | (0.016) |
|  | Urine/Serum | 0.212 | 0.187 | (0.091) |
|  | Ur/(Ur + Ser) | 0.162 | 0.141 | (0.101) |
|  | Serum/Urine | 8.361 | 12.530 | (0.090) |
|  | Ser/(Ser + Ur) | 0.838 | 0.859 | (0.101) |
| Cadmium | Serum | 1.327 | 1.278 | (<0.001) |
|  | Erythrocytes | 0.475 | 0.978 | (<0.001) |
|  | Urine | 0.165 | 0.182 | (0.376) |
|  | Erythrocytes/Serum | 0.368 | 0.967 | (<0.001) |
|  | Eryth/(Eryth + Ser) | 0.260 | 0.422 | (<0.001) |
|  | Serum/Erythrocytes | 3.318 | 1.770 | (<0.001) |
|  | Ser/(Ser + Eryth) | 0.740 | 0.578 | (<0.001) |
|  | Urine/Serum | 0.125 | 0.176 | (0.012) |
|  | Ur/(Ur + Ser) | 0.107 | 0.142 | (0.012) |
|  | Serum/Urine | 11.885 | 9.507 | (0.012) |
|  | Ser/(Ser + Ur) | 0.893 | 0.858 | (0.012) |

In men over 50 years of age in Experiment C, serum calcium was correlated with erythrocyte cadmium/(erythrocyte cadmium+serum cadmium) (defined as the counter-exchange of serum cadmium to erythrocytes) ($r=0.24$; $p=0.017$). The lower the counter-exchange of serum cadmium to erythrocytes, the lower the serum calcium, supporting the hypothesis that decreased cadmium decreases a blockage of calcium penetration into cells.

Serum calcium/erythrocyte calcium (defined as cell blockage to calcium penetration) was positively correlated with the counter-exchange of serum cadmium to erythrocytes (erythrocyte cadmium/(erythrocyte cadmium+serum cadmium)) ($r=0.22$; $p=0.025$). The lower the counter-exchange of serum cadmium to erythrocytes, the lower the blockage of calcium penetration into erythrocytes, supporting the hypothesis that decreased cadmium increases calcium penetration into erythrocytes. These data support the hypothesis that cadmium blocks calcium channels to erythrocytes, prostate cells and other cells.

Cell blockage to calcium penetration was correlated with urine cadmium/(urine cadmium+serum cadmium) (defined as the excretion of serum cadmium to urine) ($r=0.28$; $p=0.004$). The lower the excretion of serum cadmium to urine, the lower the blockage of calcium penetration into erythrocytes.

The results of these experiments provide evidence that cadmium regulates the retention of serum zinc in men and that cadmium regulates serum calcium and blockage of calcium penetration into cells. The data also provide evidence that cadmium counter-exchange from serum to erythrocytes or cadmium excretion to urine regulates retention of serum zinc from urine.

Excretion of serum calcium to urine (urine calcium/(urine calcium+serum calcium)) was correlated with urine zinc ($r=0.45$; $p<0.001$). Urine calcium was correlated with urine zinc ($r=0.49$; $p<0.001$) and urine calcium was negatively correlated with retention of serum zinc from urine (serum zinc/{serum zinc+urine zinc}) ($r=-0.46$; $p<0.001$). The greater the excretion of serum zinc to urine, the greater the excretion of serum calcium to urine.

In this study, men over 50 who had high PSA, in addition to having low serum calcium and low blockage of calcium penetration into erythrocytes, were found to have low retention of serum zinc in comparison to their counterparts with low PSA (0.349 vs 0.404, respectively; $p=0.016$)(Table 5). Men with high PSA also showed a lower retention of serum zinc from urine than men with low PSA (0.838 vs. 0.859, respectively; $p=0.101$).

Serum zinc was correlated with the counter-exchange of serum cadmium to erythrocytes ($r=0.34$; $p=0.001$), supporting the hypothesis that the counter-exchange of serum cadmium to erythrocytes regulates retention of serum zinc. Retention of serum zinc from urine was correlated with the counter-exchange of serum cadmium to erythrocytes ($r=0.17$; $p=0.090$), supporting the hypothesis that the counter-exchange of serum cadmium to erythrocytes regulates the retention of serum zinc from urine.

Excretion of serum zinc to urine was correlated with excretion of serum cadmium to urine ($r=0.40$; $p<0.001$). As the elimination of serum zinc to urine regulates the elimination of serum calcium to urine, the elimination of serum zinc to urine also regulates the elimination of serum cadmium to urine. The excretion of serum zinc to urine regulates the excretion of serum cadmium to urine.

Urine cadmium was higher in men than in stallions (Experiment A) (2.167 vs. 0.201, respectively; $p<0.001$) (Table 3). The men had a greater excretion of serum zinc to urine than did the stallions. Excretion of serum cadmium in urine was higher in the men than in the stallions (0.682 vs. 0.152, respectively; $p<0.001$). Serum zinc in men dropped significantly in the afternoon, whereas serum zinc in stallions remained constant throughout the day. Men's urine cadmium rose abruptly as their serum zinc dropped in the afternoon. Urine cadmium was found to be highest when serum zinc was the lowest.

Lower counter-exchange of serum cadmium to erythrocytes corresponds to lower exchange of serum zinc from erythrocytes and lower retention of serum zinc from urine for men with high PSA in comparison to men with low PSA. The counter-exchange of serum cadmium to erythrocytes was lower for men with high PSA than for men with low PSA (0.260 vs. 0.422, respectively; p<0.001). Also, excretion of serum cadmium to urine was lower for men with high PSA in comparison to men with low PSA (0.107 vs. 0.142, respectively; p=0.012). These data are evidence that cadmium is an essential trace element, the deficiency of which in aged men decreases their counter-exchange of serum cadmium to erythrocytes, causing decreased retention of serum zinc from urine, decreased serum zinc, decreased serum calcium, and decreased blockage of calcium penetration into erythrocytes and elevated levels of PSA.

Age was correlated with PSA in men over 50 (Experiment C) (r=0.31; p=0.002). Age and PSA shared similar negative correlations with serum calcium (r=−0.28; p=0.006; r=−0.28; p=0.005), with serum zinc (r=−0.31; p=0.002; r=−0.28; p=0.005), and with counter-exchange of serum cadmium to erythrocytes (r=−0.31; p=0.002; r=−0.41; p<0.001). Declining counter-exchange of serum cadmium to erythrocytes with increasing age parallels the declining cadmium burden in men with increasing age over 50 (Table 6). These data are evidence that cadmium deficiency causes decreased cadmium counter-exchange from serum to erythrocytes with increased aging in men. Counter-exchange of serum cadmium to erythrocytes was correlated with serum zinc (r=0.34; p=0.001) and with serum calcium (r=0.24; p=0.020). Serum zinc was correlated with serum calcium (r=0.57; p<0.001). This is evidence that decreased serum calcium represents increased cellular calcium secondary to a decreased blockage of calcium penetration into cells. There is evidence that increased calcium in prostate cells increases production and release of PSA. Decreased cadmium elimination from serum to cells (as estimated by elimination of serum cadmium to erythrocytes or urine) decreases blockage of calcium penetration into erythrocytes. As men age, elimination of serum cadmium to erythrocytes decreases (r=−0.31; p=0.002). Further, as the counter-exchange of serum cadmium to erythrocytes decreases, serum zinc (r=0.340; p=0.001) and serum calcium decreases (r=0.24; p=0.020). As serum zinc decreases, serum calcium decreases (r=0.57; p<0.001). Decreased serum calcium (r=−0.028; p=0.005), decreased serum zinc (r=−0.028; p=0.005) and decreased counter-exchange of serum cadmium to erythrocytes (r=−0.41; p<0.001) caused increased PSA.

TABLE 6

Erythrocyte Cadmium (ng/ml) in 102 Men with Low (non-bold) and High (bold) PSA (Experiment C)
Erythrocyte Cadmium

| | | | |
|---|---|---|---|
| 12.083 | 5.467 | 4.547 | n = 59 |
| 4.056 | 2.941 | 2.597 | |
| 2.553 | 2.262 | 2.182 | |
| 2.060 | 2.022 | 1.983 | |
| 1.915 | 1.844 | 1.771 | |
| 1.748 | 1.685 | 1.627 | |
| 1.620 | 1.586 | 1.515 | |
| 1.501 | 1.495 | 1.476 | |
| 1.449 | 1.398 | 1.388 | |
| 1.387 | 1.372 | 1.364 | |
| 1.319 | 1.288 | 1.245 | |
| 1.244 | 1.229 | 1.220 | |
| 1.218 | 1.215 | 1.206 | |
| 1.177 | 1.150 | 1.130 | |
| 1.128 | 1.128 | 1.113 | |
| 1.112 | 1.104 | 1.099 | |
| 1.088 | 1.084 | 1.081 | |
| 1.077 | 1.061 | 1.059 | |
| 1.045 | 1.030 | 1.019 | |
| 1.018 | 1.002 | | |
| | | 0.992 | n = 43 |
| 0.989 | 0.987 | 0.986 | |
| 0.985 | 0.962 | 0.950 | |
| 0.947 | 0.941 | 0.932 | |
| 0.930 | 0.929 | 0.928 | |
| 0.927 | 0.926 | 0.917 | |
| 0.914 | 0.914 | 0.913 | |
| 0.902 | 0.895 | 0.895 | |
| 0.887 | 0.883 | 0.880 | |
| 0.878 | 0.866 | 0.854 | |
| 0.848 | 0.846 | 0.837 | |
| 0.836 | 0.826 | 0.822 | |
| 0.819 | 0.818 | 0.784 | |
| 0.774 | 0.764 | 0.764 | |
| 0.722 | 0.319 | 0.307 | |

$\bar{X} = 1.4$
S.D. = 1.304

Erythrocyte cadmium was ordered from highest (12.083 ng/ml) to lowest (0.307 ng/ml) (Table 6). Deficiency of body cadmium was estimated to exist when erythrocyte cadmium fell below 1.0 ng/ml. Ninety five percent (41/43) of the men classified as cadmium deficient had PSA pf greater than 2.0 ng/ml. In contrast, 90% (53/59) of men not classified as cadmium deficient had PSA of less than 2.0 ng/ml.

Age was negatively correlated with retention of serum zinc from urine (r=−0.40; p<0.001), and was correlated with urine zinc (r=0.29; p=0.003), evidence that declining retention of serum zinc from urine with increasing age is caused by a declining elimination of serum cadmium caused by a deficient cadmium burden.

In Experiment D, cadmium treatment increased the counter-exchange of serum cadmium to erythrocytes in each of the three men to whom it was administered by a minimum of 116%. Average cadmium counter-exchange increased from 0.311 +/−0.166 to 0.466+/−0.077 (mean+/−S.D.). Cadmium treatment increased blockage to calcium penetration in each man by between 178–330%. Their average blockage of calcium penetration increased from 114.79+/−21.135 to 314.001+/−150.942) (mean+/−S.D.)(p=0.0492).

Example 4

A fifty-five year old man who has a PSA>2.0 ng/ml is assessed for a cadmium deficiency. Blood and urine samples are collected and analyzed for a) erythrocyte cadmium, b) the movement of cadmium between his erythrocytes and his serum (erythrocyte cadmium/(erythrocyte cadmium+serum cadmium)), and c) the movement of cadmium between his serum and urine (urine cadmium/(urine cadmium+serum cadmium)). If his cadmium level by any of these measures is found to be 15% or more below normal (i.e., if his erythrocyte cadmium level is < about 1.0 ng/ml, the concentration of erythrocyte cadmium divided by the sum of his erythrocyte cadmium concentration plus serum cadmium concentration is below about 0.44 and/or the concentration of the cadmium in his urine divided by the sum of the concentration of cadmium in his urine plus the concentration of cadmium in his serum is below about 0.17), he is examined for any other warning signs of illness and cadmium is administered at a level within the range of 0.25–2 mg/day orally, parenterally or in inhalation form for a period of 4 weeks. The specific dosage is dependent upon the form in which the cadmium is administered and the severity of the deficiency. The man is re-examined at the end of the administration period and, if any of the three measures for cadmium deficiency remains below normal, cadmium administration is continued for a further 4 weeks. This cycle is repeated until the cadmium deficiency is corrected. Once the man's levels of cadmium have been brought back within the normal range, he undergoes continued periodic monitoring and, if his cadmium levels again begin to fall, cadmium administration is reinstituted.

References

1. Hinrichs, K., "Production of Embryos by Assisted Reproduction in the Horse," *Theriogenology*, 49:13–21 (1998).
2. Baker, J. R., "A Survey of Post-Mortem Findings in 480 Horses 1958 to 1980: (1) Causes of Death," *Equine Vet. J.*, 13:43 (1981).
3. Harrison, L., "Tumors of Horses," Livestock Disease Diagnostic Center, U. Kentucky (1995).
4. "Statistics About Cancer," American Cancer Society (1996).
5. Bronson, R. T., "Variation in Age at Death of Dogs of Different Sexes and Breeds," *Am. J. Vet. Res.*, 43(11): 2057–2059 (1982).
6. Bedrak, E. and Samuels, L. T., "Steroid Biosynthesis by the Equine Testis," *Endocrinology*, 85:1186–1195 (1969).
7. Raeside, J. I., "Seasonal Changes in the Concentration of Estrogens and Testosterone in the Plasma of the Stallion," *Anim. Reprod. Sci.*, 1:205–212 (1978/1979).
8. Setchell, V. P. and Cox, J. E., "Secretion of Free and Conjugated Steroids by the Testis into the Lymph and Venous Blood," *J. Reprod. Fertil.*, Suppl. 32:123–127 (1982).
9. Thompson, D. L. et al., "Effect of Season and Artificial Photoperiod on Levels of Estradiol-17β and Estrone in Blood Serum of Stallions," *J. Anim. Sci.*, 47(l):184–187 (1978).
10. Setchell, B. P. et al., "Anatomy, Vasculature, Innervation, and Fluids of the Male Reproductive Tract," *In: The Physiology of Reproduction*, 2nd Ed., Edited by Knobil and Neill, 1:1124 (1994).
11. Claus, R. et al., "Estrogens and Prostaglandin $F_{2\alpha}$ in the Semen and Blood Plasma of Stallions," *Theriogenology*, 38:687–693 (1992).
12. Gregoraszczuk, E. et al., "The Direct Influences of Stallion Semen on Progesterone Production in Cultured Corpus Luteum Cells," *Zbl. Vet. Med. A*, 27:788–795 (1980).
13. Wodzicka-Tomaszewska, M., "Luteolytic Factor in Stallion Semen," *J. Reprod. Fertil.*, 44:297–299 (1975).
14. Woods, G. L. and Olsen, L. M., "Prostaglandin F2alpha and Prostaglandin E2 in Stallion Semen," (In Progress).
15. Clarke, E. E. et al., "Utilization of a Single Antiserum for the Direct Radioimmunoassay of Prostaglandins E and F in Semen and Prostaglandin F in Amniotic Fluid," *Prostaglandins*, 7(5):433–442 (1974).
16. Gerozissis, K. et al., "Origin of Prostaglandins in Human Semen," *Reprod. Fertil.*, 65:401–404 (1982).
17. "Low-Molecular Weight Constituents," *In: Biochemistry of Mammalian Reproduction*, Edited by Zaneveld, L. J. D. and Chatterton, R. T. pg. 103 (1982).
18. Klaassen, C. D., "The basic science of poisons," In: Amdur, M. O. and Doull, J. D. (eds.), *Caserett and Doul's Toxicology*, Fifth Edition, New York: McGraw-Hill Inc. (1996).
19. Song, M. K. et al., "Prostaglandin Interacts with Steroid Sex Hormones in the Regulation of Intestinal Zinc Transport," *Comp. Biochem. Physiol. Comp. Physiol.*, 101(3): 477–481 (1992).
20. Gonul, B. et al., "Effects of Epidermal Growth Factor on Serum Zinc and Plasma Prostaglandin E2 Levels of Mice with Pressure Sores," *Prostaglandins*, 45(2):153–157 (1993).
21. Song, M. K. et al., "Relationship Between Zinc and Prostaglandin Metabolisms in Plasma and Small Intestine of Rats," *Am. J. Clin. Nutr.*, 41(6):1201–1209 (1985).
22. Song, M. K. et al., "Metabolic Alterations of Zinc and Prostaglandins in Both Human and Animal Colonic Tumor Cells," *J. Am. Coll. Nutr.*, 14(5):473–479 (1995).
23. Oner, G. et al., "The Susceptibility to Stress-Induced Gastric Injury of Rats Exposed to Cadmium," *Biol. Trace Elem. Res.*, 47(1–3):219–223 (1995).
24. Kudo, N. et al., "Biphasic Effect of Cadmium Ions on the Secretion of Leukotriene B4 in Rabbit Alveolar Macrophages," *Arch. Toxicol.*, 70(12):801–808 (1996).
25. Zhang, Y. et al., "Secretory Leukocyte Protease Inhibitor Suppresses the Production of Monocyte Prostaglandin H Synthase-2, Prostaglandin E2, and Matrix Metalloproteinases," *J. Clin. Invest.*, 99(5): 894–900 (1997).
26. Bendvold, E. et al., "The Natural Variations in Prostaglandin Concentration in Human Seminal Fluid and its Relation to Sperm Quality," *Fertil. Steril.*, 41(5):743–747 (1984).
27. Bendvold, E. et al., "The Effect of Naproxen on the Concentration of Prostaglandins in Human Seminal Fluid," *Fertil. Steril.*, 43(6):922–926 (1985).
28. Svanborg, K. et al., "Variation in, and Inter-relationship Between, Prostaglandin Levels and Other Semen Parameters in Normal Men," *J. Androl.*, 12:411–419 (1989).
29. Colon, J. M. et al., "The Effect of Relaxin and Prostaglandin $E_2$ on the Motility of Human Spermatozoa," *Fertil. Steril.*, 46(6):1133–1139 (1986).
30. Aitken, R. J. and Kelly, R. W., "Analysis of the Direct Effects of Prostaglandins on Human Sperm Function," *J. Reprod. Fertil.*, 73:139–146 (1985).
31. Gottlieb, C. et al., "Effect of Prostaglandins on Human Sperm Function in vitro and Seminal Adenosine Triphosphate Content," *Fertil. Steril.*, 49(2):322–327 (1988).
32. Kawamori, T. et al., "Chemopreventive Activity of Celecoxib, a Specific Cyclooxygenase-2 Inhibitor, against Colon Carcinogenesis," *Cancer Res.*, 58:409–412 (1998).
33. Ablin, R. J. et al., "Effect of Human Seminal Plasma on the Lytic Activity of Natural Killer Cells and Presumptive Identification of Participant Macromolecules," *J. Reprod. Immunol.*, 24:15–21 (1990).
34. Kelly, R. W. and Critchley, H. O. D., "Immunomodulation by Human Seminal Plasma: A Benefit for Spermatozoon and Pathogen?," *Hum. Reprod.*, 12(10):2200–2207 (1997).
35. Kelly, R. W. et al., "The Immunosuppressive Contribution of Prostaglandin Components of Human Semen and their Ability to Elevate Cyclic Adenosine Monophosphate levels in Peripheral Blood Mononuclear Cells," *J. Reprod. Immunol.*, 26:31–40 (1994).

36. Miao, D. et al., "The Effects of Human Seminal Plasma and PGE2 on Mitogen Induced Proliferation and Cytokine Production of Human Splenic Lymphocytes and Peripheral Blood Mononuclear Cells," *J. Reprod. Immunol.*, 30:97–114 (1996).

37. Skibinski,G. et al., "Relative Immunosuppressive Activity of Human Seminal Prostaglandins," *J. Reprod. Immunol.*, 22:185–195 (1992).

38. Tarter, T. H. et al., "Suppression of Natural Killer Cell Activity by Human Seminal Plasma in Vitro: Identification of 19-OH-PGE as the Suppressor Factor," *J. Immunol.*, 136(8):2862–2867 (1986).

39. Omu, A. E. et al., "Treatment of Asthenozoospermia with Zinc Sulfate: Andrological, Immunological and Obstetric Outcome," *Eur. J. Obstet. Gynecol. Reprod. Biol.*, 79(2):179–184 (1998).

40. Takeda, A. et al., "Zinc Depletion Suppresses Tumor Growth in Mice," *Biol. Trace Elem. Res.*, 59(1–3):23–29 (1997).

41. Hadfield, M. G. et al., "Human Brain Tumors and Exposure to Metal and Non-Metal Elements: A Case-Control Study," *J. Environ. Pathol. Toxicol. Oncol.*, 17(1):1–9 (1998).

42. Costello, L. C. et al., "Novel Role of Zinc in the Regulation of Prostate Citrate Metabolism and its Implications in Prostate Cancer," *Prostate*, 35(4):285–296 (1998).

43. Khan, S. et al., "Zinc Protection Against Lipid Peroxidation from Cadmium," *Indian J. Exp. Biol.*, 29(9):823–825 (1991).

44. Coogan, T. P. et al., "Cadmium-Induced DNA Strand Damage in Cultured Liver Cells: Reduction in Cadmium Genotoxicity Following Zinc Pretreatment," *Toxicol. Appl. Pharmacol.*, 113(2):227–233 (1992).

45. Hartssfield, J. K. Jr. et al., "Statistical Analysis of the Effect of Cadmium and Zinc on Hamster Teratogenesis," *Biochem. Med. Metab. Biol.*, 48(2):159–173 (1992).

46. Piersma, A. H. et al., "Cadmium-Induced Inhibition of Proliferation and Differentiation of Embryonal Carcinoma Cells and Mechanistic Aspects of Protection by Zinc," *Teratology*, 48(4):335–341 (1993).

47. Wahba, Z. Z. et al., "Absence of Changes in Metallothionein RNA in the Rat Testes Made Refractory to Cadmium Toxicity by Zinc Pretreatmant," *Hum. Exp. Toxicol.*, 13(1):65–67 (1994).

48. Tanaka, M. et al., "Effect of Cadmium in the Zinc Deficient Rat," *Vet. Hum. Toxicol.*, 37(3):203–208 (1995).

49. Ohkawara, S. et al., "Interaction Between Cadmium and Zinc in the Production and Sulfation of Glycosaminoglycans in Cultured Bovine Vascular Endothelial Cells," *J. Toxicol. Environ. Health*, 47(2):183–193 (1996).

50. Mishima, A. et al., "Tolerance to Cadmium Cytotoxicity is Induced by Zinc Through Non-metallothionein Mechanisms as well as Metallothionein Induction in Cultured Cells," *Toxicology*, 118(2–3):85–92 (1997).

51. King, L. M. et al., "Murine Strain Differences and the Effects of Zinc on Cadmium Concentrations in Tissues After Acute Cadmium Exposure," *Arch. Toxicol.*, 72(10):650–655 (1998).

52. Hennig, A. et al., "Contraceptive Action of Cadmium," *Arch. Exp. Veterinarmed*, 25(5):793–798 (1971).

53. Omu, A. E. et al., "Significance of Trace Elements in Seminal Plasma of Infertile Men," *Nutrition*, 11 Suppl., 5:502–505 (1995).

54. Benoff, S. et al., "A Potential Role for Cadmium in the Etiology of Varicocele-Associated Infertility," *Fertil. Steril.*, 67(2):336–347 (1997).

55. Chia, S. M. et al., "Blood Concentrations of Lead, Cadmium, Mercury, Zinc, and Copper and Human Semen Parameters," *Arch. Androl.*, 29(2):177–183 (1992).

56. Waalkes, M. P. et al., "Further Evidence of the Tumor-Suppressive Effects of Cadmium in the B6C3F1 Mouse Liver and Lung: Late Stage Vulnerability of Tumors to Cadmium and the Role of Metallothionein," *J Pharmacol. Exp. Ther.*, 266(3):1656–1663 (1993).

57. Hayes, W. A. (ed.), *Principles and Methods of Toxicology*, Third Edition, New York:Raven Press (1994).

58. Van der Ven, H. H. et al., "Inhibition of Human Sperm Penetration into Zona-Free Hamster Oocytes by Proteinase Inhibitors," *Fertil. Steril.*, 43(4):609–616 (1985).

59. de Lamirande, E. and Gagnon, C., "Effects of Protease Inhibitors and Substrates on Motility of Mammalian Spermatozoa," *J. Cell Biol.*, 102(4):1378–1383 (1986).

60. Boettger-Tong, H. et al., "Competition Between Zonae Pellucidae and a Proteinase Inhibitor for Sperm Binding," *Biol. Reprod.*, 47(5):716–722 (1992).

61. Lee, S. L. et al., "The Involvement of Extracellular Proteinases and Proteinase Inhibitors in Mammalian Fertilization," *Biotechnol. Appl. Biochem.*, 19(Pt. 1):31–40 (1994).

62. Carroll, D. J. and Jaffe, L. A., "Proteases Stimulate Fertilization-like Responses in Starfish Eggs," *Dev. Biol.*, 170(2):690–700 (1995).

63. Ren, S. and Lien, E. J., "Development of HIV Protease Inhibitors: A Survey," *Prog. Drug Res.*, 51:1–31 (1998).

64. Ikeda, T. et al., "Anti-Invasive Activity of Synthetic Serine Protease Inhibitors and its Combined Effect with a Matrix Metalloproteinase Inhibitor," *Anticancer Res.*, 18(6A):4259–4265 (1998).

65. Kolkhorst, V. et al., "Inhibition of Tumour Cell Invasion by Protease Inhibitors: Correlation with the Protease Profile," *J. Cancer Res. Clin. Oncol.*, 124(11):598–606 (1998).

66. Waladkhani, A. R. and Clemens, M. R., "Effect of Dietary Phytochemicals on Cancer Development," *Int. J. Mol. Med.*, 1(4):747–753 (1998).

67. Kennedy, A. R., "The Bowman-Birk Inhibitor from Soybeans as an Anticarcinogenic Agent," *Am. J. Clin. Nutr.*, 68(Suppl. 6):1406S–1412S (1998).

68. Van Noorden, C. J., "Proteases and Protease Inhibitors in Cancer," *Acta. Histochem.*, 100(4):344–354 (1998).

69. Sammon, A. M., "Protease Inhibitors and Carcinoma of the Esophagus," *Cancer*, 83(3):405–408 (1998).

70. Yu, A. E. et al., "Matrix Metalloproteinases. Novel Targets for Directed Cancer Therapy," *Drugs Aging*, 11(3):229–244 (1997).

71. Rooprai, H. K. and McCormick, D., "Proteases and Their Inhibitors in Human Brain Tumours: A Review," *Anticancer Res.*, 17(6B):4151–4162 (1997).

72. Ferry, G. et al., "A Zinc Chelator Inhibiting Gelatinases Exerts Potent in Vitro Anti-Invasive Effects," *Eur. J. Pharmacol.*, 351(2):225–233 (1998).

73. Hashimoto, K. et al., "Expression of Matrix Metalloproteinase-7 and Tissue Inhibitor of Metalloproteinase-1 in Human Prostate," *J. Urol.*, 160(5):1872–1876 (1998).

74. Palm, R. and G. Hallmann, *J. Neurol. Neurosurg. Psychiatry*, 45(8):691–698 (Aug., 1982).

75. Yasui, M. and K. Ota, *Magnes. R.*, 5(4): 295–302 (Dec. 1992).

76. Wong, E. K. et al., *J. Fr. Ophthalmol.*, 6(3): 243–9 (1983).

77. Cunningham, J. J. et al., *Metabolism*, 43(12): 1558–62 (December 1994).

78. Williams, N. R., et al., *Analyst,* 120(3):887–90, (March, 1995).
79. Vivoli, G et al., "Cadmium in blood, urine and hair related to human hypertension," *J. Trace Elem Electrolytes Health Dis.,* 3(3): 139–145 (1989). PM:2535333.
80. Elinder, C. G. et al., "Cancer mortaliaty of cadmium workers," *Br. J. Ind. Med.,* 42(10):651–655 (1985). PM:4041382.
81. Habib, F. K. et al., "Metal-androgen interrelationships in carcinoma and hyperplasia of the human prostate," *J. Endocrinol.,* 71(1):133–141 (1976). PM:62007.
82. Hoffmann, L. et al., "Carcinogenic effects of cadmium on the prostate of the rat," *J. Cancer Res. Clin. Oncol.,* 109(3):193–199 (1985). PM:3409093.
83. Watanabe, T. et al., "Reduced dietary cadmium intake in past 12 years in a rural area in Japan," *Sci. Total Environ.,* 119:43–50 (1992). PM:1631532.
84. Zaridze, D. G. et al., "International trends in prostatic cancer," *Int J. Cancer,* 33(2):223–230 (1984). PM:6693200.
85. Becker, W. and Kumpulainen, J., "Contents of essential and toxic mineral elements in Swedish market-basket diets in 1987," *Br J. Nutr,* 66(2):151–160 (1991). PM:1760440.
86. Wynder, E. L. et al., "Epidemiology of cancer of the prostate," *Cancer,* 28(2):344–360 (1971). PM:5109447.
87. Tsugane, S. et al., "Cancer mortality among Japanese residents of the city of Sao Paulo, Brazil," *Int. J. Cancer,* 45(3):436–439 (1990). PM:2307534.
88. Wynder, E. L. et al., "Comparative epidemiology of cancer between the United States and Japan. A second look," *Cancer,* 67(3):746–763 (1991). PM:1985768.
89. Sandblom, G. et al., "Prostate carcinoma trends in three counties in Sweden 1987–1996: results from a poulation-based national cancer register. South-End Region Prostate Cancer Group," *Cancer,* 88(6):1445–1453 (2000). PM:10717629.
90. Hoffmann, L. et al., "Carcinogenic effects of cadmium on the prostate of the rat," *J. Cancer Res. Clin. Oncol.,* 109(3):193–199 (1985). PM:2409093.
91. Elinder, C. G. and Piscator, M., "Cadmium and zinc relationships," *Environ Health Perspect,* 25:129–132 (1978). PM:720298.
92. Lin, C. J. et al., "Differential cytotoxicity of cadmium to rat embroyonic fibroblasts and human skin fibroblasts," *Toxicol Appl Pharmacol,* 133(1):20–26 (1995). PM:7597706.
93. Puri, V. N. "Cadmium inducted hypertension," *Clin Exp Hypertens,* 21(1–2):79–84 (1999). PM:10052644.
94. Hoden, H., "Cadmium toxicology," *Lancet,* 2(7610):57 (1969). PM:4182819.
95. Shigematsu, I., "The epidemiological approach to cadmium pollution in Japan," *Ann Acad Med Singapore,* 13(2):231–236 (1984). PM:6497320.
96. Davies, N. T., "An approasal of the newer trace elements," *Philos Trans R Soc Lond B Biol Sci,* 294(1071): 171–184 (1981). PM:6118894.
97. Davies, N. T., "An appraisal of the newer trace elements," *Philos Trans R Soc Lond B Biol Sci,* 294(1071): 171–184 (1981). PM:6118894.
98. Eybl, V et al., "Effect of cadmium chelating agents on organ cadmium and race element levels in mice," *Analyst,* 123(1):25–26 (1998). PM:9581015.
99. Hongo, T., et al., "Diurnal variation of plasma minerals and trace elements in a group of Japanese male adults," *J Nutr Sci Vitaminol (Tokyo),* 39(1):33–46 (1993). PM:8509899.
100. Subramanian, K. S. and Meranger, J. E., "Diurnal variations in the concentration of cadmiumin urine," *Clin Chem,* 30(6): 1110–1111 (1984), PM:6539178.
101. Herzberg, M., et al., "Zinc excretion in osteoporotic women," *J. Bone Miner Res.,* 5(3):251–257 (1990). PM:2333784.
102. Visser, G. J. et al., "Cadmium ion is a non-competitive inhibitor of red cell (Ca(2+)-ATPase activity," *Biochim Biophys Acta.* 1152(1):26–34 (1993). PM:8399302.
103. Kukreja, S.c. et al., "Hypocalcemia in patients with prostate cancer," *Calcif Tissue Int,* 43(6):340–345 (1988). PM:3146422.
104. Cunningham, J. J., et al., "Hyperzincuria in individuals with insulin-dependent diabetes mellitus: concurrent zinc status and the effect of high-dose zinc supplementation," *Metabolism,* 43(12): 1558–1562 (1994). PM: 7990711

It is claimed:

1. A method of increasing the levels of cadmium in body fluids and tissues of a human which comprises orally administering to a human suffering from deficient levels of cadmium in his body fluids and tissues a bioavailable and physiologically acceptable cadmium salt in a series of daily doses at dose levels of about 0.5 mg to about 2 mg per day to minimize or eliminate said cadmium deficiency.

2. The method of claim 1, wherein said deficient levels of cadmium are at least about 15% below normal.

3. The method of claim 1, wherein said deficient levels of cadmium are at least about 20% below normal.

4. A method in accordance with claim 1, wherein said cadmium salt is administered in a series of daily doses at dose levels of about 0.8 mg to about 1.2 mg per day.

5. The method of claim 1, wherein said cadmium salt comprises the sulfate, nitrate, chloride or acetate cadmium salt.

6. A method in accordance with claim 4, wherein said cadmium salt is administered in a series of daily doses at dose levels of about 1 mg per day.

7. A method for correcting a cadmium deficiency in the body of a human suffering therefrom which comprises orally administering to said human a bioavailable and physiologically acceptable cadmium salt in a series of daily doses at dose levels of about 0.5 to about 2 mg per day to minimize or eliminate said cadmium deficiency.

8. A method in accordance with claim 7, wherein said cadmium salt is administered in a series of daily doses at dose levels of about 0.8 mg to about 1.2 mg per day.

9. A method of increasing the levels of cadmium in body fluids and tissues of a human which comprises parenterally administering to a human suffering from deficient levels of cadmium in his body fluids and tissues a bioavailable and physiologically acceptable cadmium salt in a series of daily doses at dose levels of about 0.025 mg to about 0.1 mg per day to minimize or eliminate said cadmium deficiency.

10. A method in accordance with claim 9, wherein said cadmium salt is administered in a series of daily doses at dose levels of about 0.04 mg to about 0.06 mg per day.

11. The method of claim 9, wherein said deficient levels of cadmium are at least about 15% below normal.

12. The method of claim 9, wherein said deficient levels of cadmium are at least about 20% below normal.

13. A method for correcting a cadmium deficiency in the body of a human suffering therefrom which comprises parenterally administering to said human a bioavailable and physiologically acceptable cadmium salt in a series of daily doses at dose levels of about 0.025 to about 0.1 mg per day to minimize or eliminate said cadmium deficiency.

14. A method in accordance with claim 13, wherein said cadmium salt is administered in a series of daily doses at dose levels of about 0.04 mg to about 0.06 mg per day.

* * * * *